US012723032B2

(12) United States Patent
Ishihara et al.

(10) Patent No.: US 12,723,032 B2
(45) Date of Patent: Sep. 1, 2026

(54) METHOD FOR PRODUCING URACIL COMPOUND

(71) Applicant: NIPPON SODA CO., LTD., Tokyo (JP)

(72) Inventors: Takuma Ishihara, Odawara (JP); Shinya Koubori, Odawara (JP); Takaaki Teranishi, Odawara (JP)

(73) Assignee: NIPPON SODA CO., LTD., Tokyo (JP)

( * ) Notice: Subject to any disclaimer, the term of this patent is extended or adjusted under 35 U.S.C. 154(b) by 414 days.

(21) Appl. No.: 18/577,779

(22) PCT Filed: Jul. 11, 2022

(86) PCT No.: PCT/JP2022/027185

§ 371 (c)(1),
(2) Date: Jan. 9, 2024

(87) PCT Pub. No.: WO2023/286719

PCT Pub. Date: Jan. 19, 2023

(65) Prior Publication Data

US 2024/0317692 A1 Sep. 26, 2024

(30) Foreign Application Priority Data

Jul. 13, 2021 (JP) ................................ 2021-115884
Aug. 12, 2021 (JP) ................................ 2021-131516

(51) Int. Cl.
*C07D 239/16* (2006.01)

(52) U.S. Cl.
CPC ................................ *C07D 239/16* (2013.01)

(58) Field of Classification Search
CPC .. C07D 239/16; C07D 239/54; C07D 405/12; C07D 417/12; C07C 275/20
See application file for complete search history.

(56) References Cited

U.S. PATENT DOCUMENTS 2,687,415 A * 8/1954 Goldberg ............ C07D 239/42 544/328

OTHER PUBLICATIONS

Jiang et al., J Am Chem Soc, 2005, 127:17412-17420 (Year: 2005).*
Majee et al., Ind J Chem, 2014, 53B:124-126 (Year: 2014).*
Piemontese et al., Eur J Med Chem, 2015, 90:583-594 (Year: 2015).*
Miyashita et al., Chem Pharm Bull, 1981, 29:3181-3190 (Year: 1981).*

* cited by examiner

*Primary Examiner* — Andrew D Kosar
*Assistant Examiner* — Jonathan D Mahlum
(74) *Attorney, Agent, or Firm* — Millen, White, Zelano & Branigan, P.C.; Brion P. Heaney

(57) ABSTRACT

An object of the present invention is to provide an industrially advantageous method for producing uracil compound, which is a production intermediate of a 2,6-dioxo-3,6-dihydropyrimidine compound, and ureidomethylene compound applicable as a raw material for uracil compounds. The present invention is characterized in that uracil compound, which is a production intermediate of a 2,6-dioxo-3,6-dihydropyrimidine compound, is produced by subjecting a compound of formula (II) below or a salt thereof to chemical reaction in the presence of an organic base or an inorganic base. In formula (II), $X^1$ represents a hydrogen atom or a substituted or unsubstituted C1-6 alkyl group, $X^2$ represents a hydrogen atom or a substituted or unsubstituted linear C1-6 alkyl group, etc., $R^1$ represents a hydrogen atom or a substituted or unsubstituted C1-6 alkyl group, etc., $R^2$ represents a hydrogen atom or a substituted or unsubstituted C1-6 alkyl group, and $R^3$ represents a substituted or unsubstituted C1-6 alkyl group, etc.

(II)

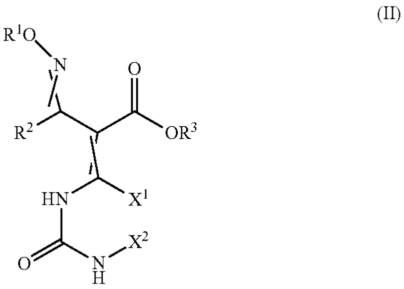

4 Claims, No Drawings

METHOD FOR PRODUCING URACIL COMPOUND

TECHNICAL FILED

The present invention relates to a method for producing uracil compound, which is a production intermediate of a 2,6-dioxo-3,6-dihydropyrimidine compound available as an active ingredient of agricultural and horticultural fungicides, and ureidomethylene compound applicable as a raw material for uracil compounds.

The present application is the U.S. National Stage of PCT/JP2022/027185, filed Jul. 11, 2022, which claims priority to Japanese unexamined Patent Application No. 2021-115884 filed on Jul. 13, 2021, and Japanese unexamined Patent Application No. 2021-131516 filed on Aug. 12, 2021, the contents of which are incorporated herein by reference.

BACKGROUND ART

In agricultural and horticultural crop cultivation, various compounds having control activity on crop diseases have been suggested. In order to practically use such a compound as an agricultural and horticultural fungicide, the compound is required not only to have sufficiently high efficacy but also to be unlikely to cause drug resistance, to be unlikely to cause phytotoxicity to plants and soil contamination, and to have low toxicity to livestock and fish.

Patent Document 1 discloses a compound of formula (A) (referred to as a "2,6-dioxo-3,6-dihydropyrimidine compound") and the like. It is disclosed that this compound has bactericidal activity, antifungal activity, and the like.

(A)

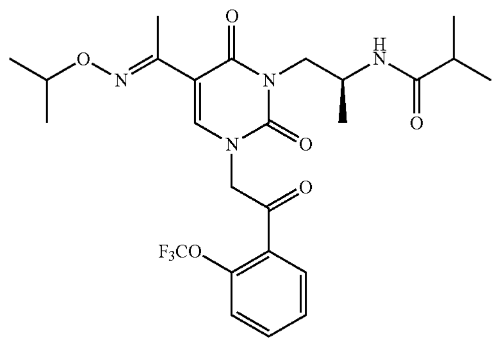

Furthermore, a compound of formula (B) and the like are disclosed as a production intermediate of that compound.

(B)

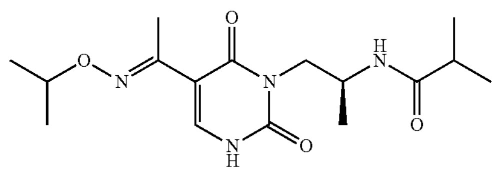

PRIOR ART DOCUMENTS

Patent Documents

Patent Document 1 WO2021/085389A

SUMMARY OF THE INVENTION

Object to be Solved by the Invention

An object of the present invention is to provide an industrially advantageous method for producing uracil compound, which is a production intermediate of a 2,6-dioxo-3,6-dihydropyrimidine compound, and a ureidomethylene compound applicable as a raw material for uracil compounds.

Means to Solve the Object

The present inventors have made intensive studies to achieve the above-mentioned objects, having completed the present invention including the following aspects.

[1] A method for producing a compound of formula (I) or a salt thereof:

(I)

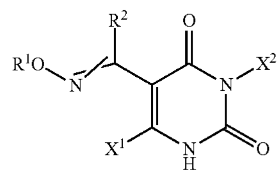

[wherein in formula(I), $X^1$ represents a hydrogen atom or a substituted or unsubstituted C1-6 alkyl group;

$R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group;

$R^2$ represents a hydrogen atom or a substituted or unsubstituted C1-6 alkyl group;

$X^2$ represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, a substituted or unsubstituted 4 to 6-membered ring heterocyclyl group, a group represented by $R^NR^NN—$, a group represented by $R^N—CO—NR^N—$, a group represented by $R^N—CO—CO—NR^N—$, a group represented by $R^N—O—CO—NR^N—$, a group represented by $R^NR^NN—CO—NR^N—$, a group represented by $R^NR^NN—CO—CO—NR^e—$, a group represented by $R^N—CS—NR^N—$, a group represented by $R^NR^NN—CS—NR^N—$, a group represented by $R^NSO_2—NR^N—$, or a group represented by $R^N—C(=NR^N)—NR^N—$;

each $R^N$ independently represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 4 to 6-membered ring heterocyclyl group, where $R^N$ and $R^N$ can together form a divalent organic group], the method comprising the step of:

subjecting a compound of formula (II) or a salt thereof to chemical reaction in the presence of an organic base or an inorganic base:

(II)

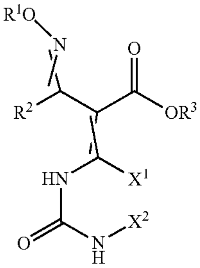

[wherein in formula (II), $R^1$, $R^2$, $X^1$, and $X^2$ represent the same meaning as those in formula (I), $R^3$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, or a substituted or unsubstituted C6-10 aryl group].

[2] The method according to [1], wherein a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group in $X^2$ and $R^N$ is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^cR^dN$—, a group represented by $R^cR^dN$—CO—, a group represented by $R^cR^dN$—$NR^d$—CO—, a group represented by $R^bSO_2$—$NR^d$—CO—, a group represented by $R^a$—CO—O—, a group represented by $R^a$—CO—$NR^e$—, a group represented by $R^a$—CO—CO—$NR^e$—, a group represented by $R^a$—CO—$NR^e$—$NR^e$—, a group represented by $R^a$—CO—$NR^e$—$NR^e$—CO—, a group represented by $R^b$—O—CO—O—, a group represented by $R^b$—O—CO—$NR^e$—, a group represented by $R^cR^dN$—CO—O—, a group represented by $R^cR^dN$—CO—$NR^e$—, a group represented by $R^cR^dN$—CO—CO—$NR^e$—, a group represented by $R^a$—CS—$NR^e$—, a group represented by $R^cR^dN$—CS—$NR^e$—, a group represented by $R^bSO_2$—$NR^e$—, a group represented by $R^cR^dN$—$SO_2$—, a group represented by $R^aO$—N═$CR^f$—, a group represented by $R^hR^iC$═N—O—, a group represented by $R^a$—C(═$NR^g$)—$NR^e$—, a group represented by $R^cR^dN$—C(═$NR^g$)—, a group represented by $R^hR^iS$(═O)═N—CO—, and a group represented by $R^hR^iS$═N—CO—;

each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group, each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^c$ and $R^d$ can together form a divalent organic group, each $R^e$ independently represents a hydrogen atom, a substituted or unsubstituted C1-6 alkyl group, a substituted or unsubstituted C1-6 alkoxy group, or a substituted or unsubstituted C6-10 aryl group, $R^f$ represents a hydrogen atom, an amino group, or a substituted or unsubstituted C1-6 alkyl group, each $R^9$ independently represents a hydrogen atom, a substituted or unsubstituted C1-6 alkyl group, or a substituted or unsubstituted C6-10 aryl group, each $R^h$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group, where $R^h$ and $R^i$ can together form a divalent organic group; and when two or more substituents are present on the linear C1-6 alkyl group, two of the substituents can together form a divalent organic group.

[3] A compound of formula (II) or a salt thereof:

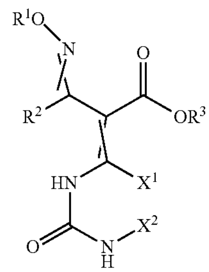

(II)

[wherein in formula(II), $X^1$ represents a hydrogen atom or a substituted or unsubstituted C1-6 alkyl group;

$R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, $R^2$ represents a hydrogen atom or a substituted or unsubstituted C1-6 alkyl group;

$X^2$ represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, a substituted or unsubstituted 4 to 6-membered ring heterocyclyl group, a group represented by $R^NR^NN$—, a group represented by $R^N$—CO—$NR^N$—, a group represented by $R^N$—CO—CO—$NR^N$—, a group represented by $R^N$—O—CO—$NR^N$—, a group represented by $R^NR^NN$—CO—$NR^N$—, a group represented by $R^NR^NN$—CO—CO—$NR^e$—, a group represented by $R^N$—CS—$NR^N$—, a group represented by $R^NR^NN$—CS—$NR^N$—, a group represented by $R^NSO_2$—$NR^N$—, or a group represented by $R^N$—C(═$NR^N$)—$NR^N$—;

each $R^N$ independently represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 4 to 6-membered ring heterocyclyl group, where $R^N$ and $R^N$ can together form a divalent organic group; and $R^3$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, or a substituted or unsubstituted C6-10 aryl group].

[4] The compound according to [3] or a salt thereof, wherein a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group in $X^2$ and $R^N$ is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^cR^dN$—, a group represented by $R^cR^dN$—CO—, a group represented by $R^cR^dN$—$NR^d$—CO—, a group represented by $R^bSO_2$—$NR^d$—CO—, a group represented by $R^a$—CO—O—, a group represented by $R^a$—CO—$NR^e$—, a group represented by $R^a$—CO—CO—$NR^e$—, a group represented by $R^a$—CO—$NR^e$—$NR^e$—, a group represented by $R^a$—CO—$NR^e$—$NR^e$—CO—, a group represented by $R^b$—O—CO—O—, a group represented by $R^b$—O—CO—$NR^e$—, a group represented by $R^cR^dN$—CO—O—, a group represented by $R^cR^dN$—CO—$NR^e$—, a group represented by $R^cR^dN$—CO—CO—$NR^e$—, a group represented by $R^a$—CS—$NR^e$—, a group represented by $R^cR^dN$—CS—$NR^e$—, a group represented by $R^bSO_2$—$NR^e$—, a group represented by $R^cR^dN$—$SO_2$—, a group represented by $R^aO$—N═$CR^f$—, a group represented by $R^hR^iC$═N—O—, a group represented by $R^a$—C(═$NR^g$)—$NR^e$—, a group represented by $R^cR^dN$—C(═$NR^g$)—, a group represented by $R^hR^iS$(═O)═N—CO—, and a group represented by $R^hR^iS$═N—CO—;

each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group, each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^c$ and $R^d$ can together form a divalent organic group, each $R^e$ independently represents a hydrogen atom, a substituted or unsubstituted C1-6 alkyl group, a substituted or unsubstituted C1-6 alkoxy group, or a substituted or unsubstituted C6-10 aryl group, $R^f$ represents a hydrogen atom, an amino group, or a substituted or unsubstituted C1-6 alkyl group, each $R^9$ independently represents a hydrogen atom, a substituted or unsubstituted C1-6 alkyl group, or a substituted or unsubstituted C6-10 aryl group, each $R^h$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group, where $R^h$ and $R^i$ can together form a divalent organic group; and when two or more substituents are present on the linear C1-6 alkyl group, two of the substituents can together form a divalent organic group.

Effect of the Invention

Uracil compound, which is a production intermediate of a 2,6-dioxo-3,6-dihydropyrimidine compound, can be produced in an industrially advantageous manner by using a ureidomethylene compound as a raw material.

MODE OF CARRYING OUT THE INVENTION

[Uracil Compound and Ureidomethylene Compound]

The present invention is a method for producing a compound of formula (I) or a salt thereof (referred to as "uracil compound"), the method comprising subjecting a compound of formula (II) or a salt thereof (referred to as a "ureidomethylene compound") to chemical reaction in the presence of an organic base or an inorganic base.

Formula (I) is shown in the following:

(I)

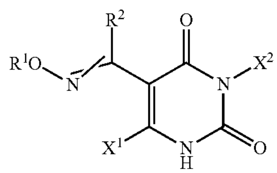

Secondly, formula (II) is shown:

(II)

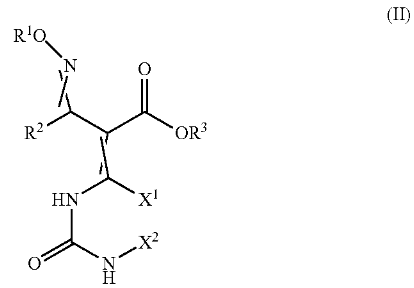

The meaning of symbols in formula (I) and formula (II) will be described in the subsequent part.

[$X^1$]

$X^1$ represents a hydrogen atom or a substituted or unsubstituted C1-6 alkyl group.

[$R^1$]

$R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

[$R^2$]

$R^2$ represents a hydrogen atom or a substituted or unsubstituted C1-6 alkyl group.

[$X^2$, $R^N$]

$X^2$ represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, a substituted or unsubstituted 4 to 6-membered ring heterocyclyl group, a group represented by $R^NR^NN$—, a group represented by $R^N$—CO—$NR^N$—, a group represented by $R^N$—CO—CO—$NR^N$—, a group represented by $R^N$—O—CO—$NR^N$—, a group represented by $R^NR^NN$—CO—$NR^N$—, a group represented by $R^NR^NN$—CO—CO—$NR^e$—, a group represented by $R^N$—CS—$NR^N$—, a group represented by $R^NR^NN$—CS—$NR^N$—, a group represented by $R^NSO_2$—$NR^N$—, or a group represented by $R^N$—C(═$NR^N$)—$NR^N$—; and each $R^N$ independently represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 4 to 6-membered ring heterocyclyl group.

Here, $R^N$ and $R^N$ can together form a divalent organic group.

[$R^3$]

$R^3$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, or a substituted or unsubstituted C6-10 aryl group.

Specific Examples of Substituents on $R^1$, $R^2$, $R^3$, $R^N$, $X^1$, and $X^2$ The "C1-6 alkyl group" can be a linear chain or can be a branched chain. Examples of the "C1-6 alkyl group" can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

As the "C2-6 alkenyl group", a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, or the like can be exemplified.

As the "C2-6 alkynyl group", an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group, or the like can be exemplified.

Examples of the "C3-6 cycloalkyl group" can include a cyclopropyl group, a cyclobutyl group, a cyclopentyl group, and a cyclohexyl group.

Examples of the "C6-10 aryl group" can include a phenyl group, a naphthyl group, an indanyl group, an indenyl group, and a tetralinyl group.

The "4 to 6-membered ring heterocyclyl group" is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms can be the same or different. Examples of the "4 to 6-membered ring heterocyclyl group" can include a 4 to 6-membered ring saturated heterocyclyl group, a 5 to 6-membered ring heteroaryl group, and a 5 to 6-membered ring partially unsaturated heterocyclyl group. The same is also applied to the "5 to 6-membered ring heterocyclyl group", except for the description regarding 4-membered rings.

Examples of the 4-membered ring saturated heterocyclyl group can include an azetidinyl group and an oxetanyl group.

Examples of the 5 to 6-membered ring saturated heterocyclyl group can include a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 6-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered ring heteroaryl group such as a pyridyl group, a pyrazinyl group, a pyrimidinyl group, a pyridazinyl group, and a triazinyl group.

Examples of the 5 to 6-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, an oxazolinyl group, and an isoxazolinyl group; and a 6-membered ring partially unsaturated heterocyclyl group such as a dihydropyranyl group.

Examples of the "linear C1-6 alkyl group" can include a methyl group, an ethyl group, a n-propyl group, a n-butyl group, a n-pentyl group, and a n-hexyl group.

Examples of the "linear C2-6 alkenyl group" can include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, and a 5-hexenyl group.

Examples of the "linear C2-6 alkynyl group" can include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, and a 1-hexynyl group.

The substituent on the "C1-6 alkyl group", the "C2-6 alkenyl group", or the "C2-6 alkynyl group" is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

The substituent on the "C3-6 cycloalkyl group", the "C6-10 aryl group", or the "5 to 6-membered ring heterocyclyl group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Further, as the substituent on the "C3-6 cycloalkyl group", or the "5 to 6-membered ring heterocyclyl group", an oxo group is also preferred.

Examples of the "divalent organic group that can be formed together" can include a substituted or unsubstituted C2-5 alkylene group, a substituted or unsubstituted C1-3 alkyleneoxy C1-3 alkylene group, a substituted or unsubstituted C1-3 alkylenethio C1-3 alkylene group, or a substituted or unsubstituted C1-3 alkyleneimino C1-3 alkylene group.

Further examples can include a silicon-containing divalent hydrocarbon group such as $—CH_2CH_2—Si(CH_3)_2—CH_2CH_2—$.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

Examples of the "C1-3 alkylenethio C1-3 alkylene group" can include a dimethylenethiodimethylene group.

Examples of the "C1-3 alkyleneimino C1-3 alkylene group" can include a dimethyleneiminodimethylene group.

Here, the imino group of the "C1-3 alkyleneimino C1-3 alkylene group" means —NH—.

The substituent on the "C2-5 alkylene group", the "C1-3 alkyleneoxy C1-3 alkylene group", the "C1-3 alkylenethio C1-3 alkylene group", and the "C1-3 alkyleneimino C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; a methylidene group; or a C1-6 haloalkyl group such as a chloromethyl group, a chloroethyl group, a trifluoromethyl group, a 1,2-dichloro-n-propyl group, or a 1-fluoro-n-butyl group.

[G]

As a substituent on the "linear C1-6 alkyl group", a substituent on the "linear C2-6 alkenyl group", a substituent on the "linear C2-6 alkynyl group", a substituent on the "C3-6 cycloalkyl group", a substituent on the "C6-10 aryl group", or a substituent on the "4 to 6-membered ring heterocyclyl group", one or more substituents selected from a group of substituents below (hereinbelow, this substituent referred to by a symbol "G") or the like can be exemplified.

When two or more substituents (G) are present, two of the substituents can together form a divalent organic group.

The group of substituents is shown below:

a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a—CO—$, a carboxy group, a group represented by $R^b—O—CO—$, a group represented by $R^cR^dN—$, a group represented by $R^cR^dN—CO—$, a group represented by $R^cR^dN—NR^d—CO—$, a group represented by $R^bSO_2—NR^d—CO—$, a group represented by $R^a—CO—O—$, a group represented by $R^a—CO—NR^e—$, a group represented by $R^a—CO—CO—NR^e—$, a group represented by $R^a—CO—NR^e—NR^e—$, a group represented by $R^a—CO—NR^e—NR^e—CO—$, a group represented by $R^b—O—CO—O—$, a group represented by $R^b—O—CO—NR^e—$, a group represented by $R^cR^dN—CO—O—$, a group represented by $R^cR^dN—CO—NR^e—$, a group represented by $R^cR^dN—CO—CO—NR^e—$, a group represented by $R^a—CS—NR^e—$, a group represented by $R^cR^dN—CS—NR^e—$, a group represented by $R^bSO_2—NR^e—$, a group represented by $R^cR^dN—SO_2—$, a group represented by $R^aO—N{=}CR^f—$, a group represented by $R^hR^jC{=}N—O—$, a group represented by $R^a—C({=}NR^g)—NR^e—$, a group represented by $R^cR^dN—C({=}NR^g)—$, a group represented by $R^hR^iS({=}O){=}N—CO—$, and a group represented by $R^hR^iS{=}N—CO—$.

In the group of substituents described above, each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group.

Each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^c$ and $R^d$ can together form a divalent organic group.

Each $R^e$ independently represents a hydrogen atom, a substituted or unsubstituted C1-6 alkyl group, a substituted or unsubstituted C1-6 alkoxy group, or a substituted or unsubstituted C6-10 aryl group.

$R^f$ represents a hydrogen atom, an amino group, or a substituted or unsubstituted C1-6 alkyl group.

Each $R^9$ independently represents a hydrogen atom, a substituted or unsubstituted C1-6 alkyl group, or a substituted or unsubstituted C6-10 aryl group.

Each $R^h$ independently represents a substituted or unsubstituted C1-6 alkyl group or a substituted or unsubstituted C6-10 aryl group.

Each $R^i$ independently represents a substituted or unsubstituted C1-6 alkyl group or a substituted or unsubstituted C6-10 aryl group, where $R^h$ and $R^i$ can together form a divalent organic group.

Examples of the "halogeno group" in G can include a fluoro group, a chloro group, a bromo group, and an iodo group.

The "C1-6 alkyl group" in G can be a linear chain or can be a branched chain. Examples of the "C1-6 alkyl group" can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group. Examples of the "C2-6 alkenyl group" can include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group. Examples of the "C2-6 alkynyl group" can include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C1-6 alkoxy group" in G can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group. Examples of the "C2-6 alkenyloxy group" can include a vinyloxy group, an allyloxy group, a propenyloxy group, and a butenyloxy group. Examples of the "C2-6 alkynyloxy group" can include an ethynyloxy group and a propargyloxy group.

Examples of the "C1-6 alkylthio group" in G can include a methylthio group, an ethylthio group, a n-propylthio group, a n-butylthio group, a n-pentylthio group, a n-hexylthio group, and an i-propylthio group. Examples of the "C1-6 alkylsulfinyl group" can include a methylsulfinyl group, an ethylsulfinyl group, and a t-butylsulfinyl group. Examples of the "C1-6 alkylsulfonyl group" can include a methylsulfonyl group, an ethylsulfonyl group, and a t-butylsulfonyl group.

The substituent on the "C1-6 alkyl group", the "C2-6 alkenyl group", the "C2-6 alkynyl group", the "C1-6 alkoxy group", the "C2-6 alkenyloxy group", the "C2-6 alkynyloxy group", the "C1-6 alkylthio group", the "C1-6 alkylsulfinyl group", or the "C1-6 alkylsulfonyl group" in G is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in G can include a cyclopropyl group, a cyclobutyl group, a cyclopentyl group, and a cyclohexyl group. Examples of the "C3-6 cycloalkyloxy group" can include a cyclopropyloxy group, a cyclobutyloxy group, a cyclopentyloxy group, and a cyclohexyloxy group.

Examples of the "C6-10 aryl group" in G can include a phenyl group and a naphthyl group. Examples of the "C6-10 aryloxy group" can include a phenoxy group and a naphthoxy group.

Examples of the "C6-10 arylthio group" in G can include a phenylthio group and a naphthylthio group. Examples of the "C6-10 arylsulfinyl group" can include a phenylsulfinyl group and a naphthylsulfinyl group. Examples of the "C6-10 arylsulfonyl group" can include a phenylsulfonyl group and a naphthylsulfonyl group.

The "3 to 10-membered ring heterocyclyl group" in G is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms can be the same or different. The group can be either monocyclic or polycyclic.

Examples of the "3 to 10-membered ring heterocyclyl group" can include a 3 to 6-membered ring saturated heterocyclyl group, a 5 to 10-membered ring heteroaryl group, and a 5 to 10-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 10-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered ring heteroaryl group such as a pyridyl group, a pyrazinyl group, a pyrimidinyl group, a pyridazinyl group, and a triazinyl group; a 9-membered heteroaryl group such as an indolyl group, an isoindolyl group, a benzofuranyl group, a benzothienyl group, an indazolyl group, a benzimidazolyl group, a benzoxazolyl group, a benzisoxazolyl group, a benzothiazolyl group, and a benzisothiazolyl group; and a 10-membered heteroaryl group such as a quinolinyl group, an isoquinolinyl group, a cinnolinyl group, a phthalazinyl group, a quinazolinyl group, and a quinoxalinyl group.

Examples of the 5 to 10-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, an oxazolinyl group, and an isoxazolinyl group; a 6-membered ring partially unsaturated heterocyclyl group such as a dihydropyranyl group; a 9-membered ring partially unsaturated heterocyclyl group such as an indolinyl group, an isoindolinyl group, a 2,3-dihydrobenzofuranyl group, and a 1,3-dihydrobenzofuranyl group; and a 10-membered ring partially unsaturated heterocyclyl group such as a 1,2,3,4-tetrahydroquinolinyl group.

The "3 to 10-membered ring heterocyclyloxy group" in G has a structure in which a 3 to 10-membered ring heterocyclyl group is bonded to an oxy group. Specifically, a thiazolyloxy group, a pyridyloxy group, or the like can be exemplified.

The substituent on the "C3-6 cycloalkyl group", the "C3-6 cycloalkyloxy group", the "C6-10 aryl group", the "C6-10 aryloxy group", the "C6-10 arylthio group", the "C6-10 arylsulfinyl group", the "C6-10 arylsulfonyl group", the "3 to 10-membered ring heterocyclyl group", or the "3 to 10-membered ring heterocyclyloxy group" in G is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as 2-chloro-n-propoxy group, a 2,3-dichlorobutoxy group, or a trifluoromethoxy group; a C3-6 cycloalkyl C1-6 alkoxy group; a C6-10 aryl C1-6 alkoxy group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 5-membered ring heteroaryl C1-6 alkoxy group; a (5-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 6-membered ring heteroaryl C1-6 alkoxy group; a (6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C1-6 haloalkylthio group such as a trifluoromethylthio group or a 2,2,2-trifluoroethylthio group; a C1-6 haloalkylsulfinyl group such as a trifluoromethylsulfinyl group or a 2,2,2-trifluoroethylsulfinyl group; a C1-6 haloalkylsulfonyl group such as a trifluoromethylsulfonyl group or a 2,2,2-trifluoroethylsulfonyl group; a C3-6 cycloalkyl group such as a cyclopropyl group or a cyclobutyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C3-6 cycloalkenyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; 3 to 4-membered ring saturated heterocyclyl group such as an aziridinyl group, an epoxy group, an azetidinyl group, or an oxetanyl group; a 3 to 4-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5 to 6-membered ring saturated heterocyclyl group such as a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, or a dioxanyl group; a 5 to 6-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; a 5-membered ring partially unsaturated heterocyclyl group such as a pyrrolinyl group, a dihydrofuranyl group, an imidazolinyl group, a pyrazolinyl group, or an oxazolinyl group, or an isoxazolinyl group; a 5-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; a 6-membered ring partially unsaturated heterocyclyl group such as a dihydropyranyl group; a 6-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; a group represented by $R^{G1}$—CO— (wherein $R^{G1}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{G1}$ below.)

- a carboxy group;
- a group represented by $R^{G2}$—O—CO— (wherein $R^{G2}$ represents a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{G2}$ below.);
- a group represented by $R^{G1}R^{G1}$N— (wherein $R^{G1}$'s in the formula can be the same or different; $R^{G1}$'s can together form a trimethylene group, a tetramethylene group, a pentamethylene group, or a dimethyleneoxydimethylene group.);
- a group represented by $R^{G1}R^{G1}$N—CO— (wherein $R^{G1}$'s in the formula can be the same or different; $R^{G1}$'s can together form a trimethylene group, a tetramethylene group, a pentamethylene group, or a dimethyleneoxydimethylene group.);
- a group represented by $R^{G1}$—CO—O—;
- a group represented by $R^{G1}$—CO—$NR^{G3}$— (wherein $R^{G3}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; or a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; the same applies to $R^{G3}$ below.);
- a group represented by $R^{G2}$—O—CO—O—;
- a group represented by $R^{G2}$—O—CO—$NR^{G3}$—;
- a group represented by $R^{G1}R^{G1}$N—CO—O— (wherein $R^{G1}$'s in the formula can be the same or different; $R^{G1}$'s can together form a trimethylene group, a tetramethylene group, a pentamethylene group, or a dimethyleneoxydimethylene group.);
- a group represented by $R^{G1}R^{G1}$N—CO—$NR^{G3}$— (wherein $R^{G1}$'s in the formula can be the same or different; $R^{G1}$'s can together form a trimethylene group, a tetramethylene group, a pentamethylene group, or a dimethyleneoxydimethylene group.);
- a group represented by $R^{G2}SO_2$—$NR^{G3}$—;
- a group represented by $R^{G1}R^{G1}$N—$SO_2$— (wherein $R^{G1}$'s in the formula can be the same or different; $R^{G1}$'s can together form a trimethylene group, a tetramethylene group, a pentamethylene group, or a dimethyleneoxydimethylene group.);
- a group represented by $R^{G1}$—O—N=C($R^{G4}$)— (wherein $R^{G4}$ represents a hydrogen atom or a C1-6 alkyl group.);
- a group represented by $(R^{G1})_2$C=N—O— (wherein $R^{G1}$'s in the formula can be the same or different; $R^{G1}$'s can together form a trimethylene group, a tetramethylene group, a pentamethylene group, or a dimethyleneoxydimethylene group.);
- a pentafluorosulfanyl group, a nitro group, or a cyano group.

Further, as the substituent on the "C3-6 cycloalkyl group", the "C3-6 cycloalkyloxy group", the "3 to 10-membered ring heterocyclyl group", or the "3 to 10-membered ring heterocyclyloxy group", an oxo group is also preferred.

In the "group represented by $R^a$—CO—" in G, $R^a$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group.

Examples of the "C1-6 alkyl group" in $R^a$ can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group. Examples of the "C2-6 alkenyl group" can include a vinyl group and a 1-propenyl group. Examples of the "C2-6 alkynyl group" can include an ethynyl group and a 1-propynyl group.

The substituent on the "C1-6 alkyl group", the "C2-6 alkenyl group", or the "C2-6 alkynyl group" in $R^a$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as 2-chloro-n-propoxy group, a 2,3-dichlorobutoxy group, or a trifluoromethoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a carboxy group; a C1-6 alkoxycarbonyl group such as a methoxycarbonyl group, an ethoxycarbonyl group, a n-propoxycarbonyl group, an i-propoxycarbonyl group, a n-butoxycarbonyl group, or a t-butoxycarbonyl group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in $R^a$ can include a cyclopropyl group, a cyclobutyl group, a cyclopentyl group, and a cyclohexyl group. Examples of the "C6-10 aryl group" can include a phenyl group, a naphthyl group, an indenyl group, an indanyl group, and a tetralinyl group.

The "3 to 10-membered ring heterocyclyl group" in $R^a$ is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms can be the same or different. The group can be either monocyclic or polycyclic.

Examples of the "3 to 10-membered ring heterocyclyl group" can include a 3 to 6-membered ring saturated heterocyclyl group, a 5 to 10-membered ring heteroaryl group, and a 5 to 10-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 10-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered ring heteroaryl group such as a pyridyl group, a pyrazinyl group, a pyrimidinyl group, a pyridazinyl group, and a triazinyl group; a 9-membered heteroaryl group such as an indolyl group, an isoindolyl group, a benzofuranyl group, a benzothienyl group, an indazolyl group, a benzimidazolyl group, a benzoxazolyl group, a benzisoxazolyl group, a benzothiazolyl group, and a benzisothiazolyl group; and a 10-membered heteroaryl group such as a quinolinyl group, an isoquinolinyl group, a cinnolinyl group, a phthalazinyl group, a quinazolinyl group, and a quinoxalinyl group.

Examples of the 5 to 10-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, an oxazolinyl group, and an isoxazolinyl group; a 6-membered ring partially unsaturated heterocyclyl group such as a dihydropyranyl group; a 9-membered ring partially unsaturated heterocyclyl group such as an indolinyl group, an isoindolinyl group, a 2,3-dihydrobenzofuranyl group, and a 1,3-dihydrobenzofuranyl group; and a 10-membered ring partially unsaturated heterocyclyl group such as a 1,2,3,4-tetrahydroquinolinyl group.

The substituent on the "C3-6 cycloalkyl group", the "C6-10 aryl group", or the "3 to 10-membered ring heterocyclyl group" in $R^a$ is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl C1-6 alkoxy group; a C6-10 aryl C1-6 alkoxy group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 5-membered ring heteroaryl C1-6 alkoxy group; a (5-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 6-membered ring heteroaryl C1-6 alkoxy group; a (6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C1-6 haloalkylthio group such as a trifluoromethylthio group or a 2,2,2-trifluoroethylthio group; a C1-6 haloalkylsulfinyl group such as a trifluoromethylsulfinyl group or a 2,2,2-trifluoroethylsulfinyl group; a C1-6 haloalkylsulfonyl group such as a trifluoromethylsulfonyl group or a 2,2,2-trifluoroethylsulfonyl group; a C3-6 cycloalkyl group such as a cyclopropyl group, a cyclobutyl group, or a cyclopentyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C3-6 cycloalkenyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 3 to 4-membered ring saturated heterocyclyl group such as an aziridinyl group, an epoxy group, an azetidinyl group, or an oxetanyl group; a 3 to 4-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5 to 6-membered ring saturated heterocyclyl group such as a pyrrolidinyl group, a tetrahydrofuranyl group, a thiazolidinyl group, a tetrahydro-2H-pyranyl group, a piperidyl group, a piperazinyl group, morpholinyl group, a dioxolanyl group, or a dioxanyl group; a 5 to 6-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; a 5-membered ring partially unsaturated heterocyclyl group such as a pyrrolinyl group, a dihydrofuranyl group, an imidazolinyl group, a pyrazolinyl group, an oxazolinyl group, or an isoxazolinyl group; a 5-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; a 6-membered ring partially unsaturated heterocyclyl group such as a dihydropyranyl group; a 6-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group;

a group represented by $R^{q1}$—CO— (wherein $R^{q1}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group;

a C2-6 haloalkynyl group; a C3-6 cycloalkyl group; C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; a 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{q1}$ below.);

a carboxy group;

a group represented by $R^{q2}$—O—CO— (wherein $R^{q2}$ represents a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; a 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{q2}$ below.);

a group represented by $R^{q1}R^{q1}N$— (wherein $R^{q1}$'s in the formula can be the same or different; $R^{q1}$'s can together form a trimethylene group, a tetramethylene group, a pentamethylene group, or a dimethyleneoxydimethylene group.);

a group represented by $R^{q1}R^{q1}N$—CO— (wherein $R^{q1}$'s in the formula can be the same or different; $R^{q1}$'s can together form a trimethylene group, a tetramethylene group, a pentamethylene group, or a dimethyleneoxydimethylene group.);

a group represented by $R^{q1}$—CO—O—;

a group represented by $R^{q1}$—CO—$NR^{q3}$— (wherein $R^{q3}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; or a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; the same applies to $R^{q3}$ below.);

a group represented by $R^{q2}$—O—CO—O—;

a group represented by $R^{q2}$—O—CO—$NR^{q3}$—;

a group represented by $R^{q1}R^{q1}N$—CO—O— (wherein $R^{q1}$'s in the formula can be the same or different; $R^{q1}$'s can together form a trimethylene group, a tetramethylene group, a pentamethylene group, or a dimethyleneoxydimethylene group.);

a group represented by $R^{q1}R^{q1}N$—CO—$NR^{q3}$— (wherein $R^{q1}$'s in the formula can be the same or different; $R^{q1}$'s can together form a trimethylene group, a tetramethylene group, a pentamethylene group, or a dimethyleneoxydimethylene group.);

a group represented by $R^{q2}SO_2$—$NR^{q3}$—;

a group represented by $R^{q1}R^{q1}N$—$SO_2$— (wherein $R^{q1}$'s in the formula can be the same or different; $R^{q1}$'s can together form a trimethylene group, a tetramethylene group, a pentamethylene group, or a dimethyleneoxydimethylene group.);

a group represented by $R^{q1}$—O—N═C($R^{q4}$)— (wherein $R^{q4}$ represents a hydrogen atom or a C1-6 alkyl group.);

a group represented by $(R^{q1})_2C$═N—O— (wherein $R^{q1}$'s in the formula can be the same or different; $R^{q1}$'s can together form a trimethylene group, a tetramethylene group, a pentamethylene group, or a dimethyleneoxydimethylene group.);

a pentafluorosulfanyl group, a nitro group, or a cyano group.

Further, as the substituent on the "C3-6 cycloalkyl group" or the "3 to 10-membered ring heterocyclyl group", an oxo group is also preferred.

Specific examples of the "group represented by $R^a$—CO—" can include a formyl group, an acetyl group, and an i-propylcarbonyl group.

In "the group represented by $R^b$—O—CO—" in G, $R^b$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Specific examples of the substituent in $R^b$ can include the same as those exemplified for $R^a$.

Specific examples of the "group represented by $R^b$—O—CO—" can include a methoxycarbonyl group, an ethoxycarbonyl group, a n-propoxycarbonyl group, an i-propoxycarbonyl group, a n-butoxycarbonyl group, and a t-butoxycarbonyl group.

In the "group represented by $R^cR^dN$—" in G, $R^c$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^d$ represents a hydrogen atom, a substituted or unsubstituted C1-6 alkyl group, a substituted or unsubstituted C1-6 alkoxy group, or a substituted or unsubstituted C6-10 aryl group.

Specific examples of the substituent in $R^c$ or $R^d$ can include the same as those exemplified for $R^a$.

Examples of the "C1-6 alkoxy group" in $R^d$ can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

The substituent on the "C1-6 alkoxy group" in $R^d$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, or a cyclopentyl group, cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; or a cyano group.

Here, $R^c$ and $R^d$ can together form a divalent organic group.

Examples of the divalent organic group that can be formed can include a substituted or unsubstituted C2-5 alkylene group, a substituted or unsubstituted C1-3 alkyleneoxy C1-3 alkylene group, a substituted or unsubstituted C1-3 alkylenethio C1-3 alkylene group, or a substituted or unsubstituted C1-3 alkyleneimino C1-3 alkylene group.

Further examples can include a silicon-containing divalent hydrocarbon group such as —$CH_2CH_2$—$Si(CH_3)$ 2-$CH_2CH_2$—.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

Examples of the "C1-3 alkylenethio C1-3 alkylene group" can include a dimethylenethiodimethylene group.

Examples of the "C1-3 alkyleneimino C1-3 alkylene group" can include a dimethyleneiminodimethylene group.

Here, the imino group of the "C1-3 alkyleneimino C1-3 alkylene group" means —NH—.

The substituent on the "C2-5 alkylene group", the "C1-3 alkyleneoxy C1-3 alkylene group", the "C1-3 alkylenethio C1-3 alkylene group", and the "C1-3 alkyleneimino C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; a methylidene group; or a C1-6 haloalkyl group such as a chloromethyl group, a chloroethyl group, a trifluoromethyl group, a 1,2-dichloro-n-propyl group, or a 1-fluoro-n-butyl group.

Specific examples of the "group represented by $R^cR^dN$—" can include an amino group, a methylamino group, a dimethylamino group, and an i-propylamino group.

In the "group represented by $R^cR^dN$—CO—" in G, $R^c$ and $R^d$ represent the same meaning as those in the above "group represented by $R^cR^dN$—".

Specific examples of the "group represented by $R^cR^dN$—CO—" can include a carbamoyl group, a N,N-dimethylaminocarbonyl group, a N-(i-propyl) aminocarbonyl group, and a N-(i-propyl)-N-methylaminocarbonyl group.

In the "group represented by $R^cR^dN$—$NR^d$—CO—" in G, $R^c$ and $R^d$ represent the same meaning as those in the above "group represented by $R^cR^dN$—".

Specific examples of the "group represented by $R^cR^dN$—$NR^d$—CO—" can include a 2,2-dimethylhydrazine-1-carbonyl group.

In the "group represented by $R^bSO_2$—$NR^d$—CO—" in G, $R^b$ represents the same meaning as that in the above "group represented by $R^b$—O—CO—", and $R^d$ represents the same meaning as that in the above "group represented by $R^cR^dN$—".

Specific examples of the "group represented by $R^bSO_2$—$NR^d$—CO—" can include a (methylsulfonyl)carbamoyl group, a (cyclopropylsulfonyl)carbamoyl group, and a ((1-methylcyclopropyl)sulfonyl)carbamoyl group.

In the "group represented by $R^a$—CO—O—" in G, $R^a$ represents the same meaning as that in the above "group represented by $R^a$—CO—".

Specific examples of the "group represented by $R^a$—CO—O—" can include an acetyloxy group.

In the "group represented by $R^a$—CO—$NR^e$—" in G, $R^a$ represents the same meaning as that in the above "group represented by $R^a$—CO—".

$R^e$ represents a hydrogen atom, a substituted or unsubstituted C1-6 alkyl group, a substituted or unsubstituted C1-6 alkoxy group, or a substituted or unsubstituted C6-10 aryl group.

Specific examples of the substituent in $R^e$ can include the same as those exemplified for $R^a$.

Specific examples of the "group represented by $R^a$—CO—$NR^e$—" can include an acetylamino group, a propionylamino group, a butyrylamino group, and an i-propylcarbonylamino group.

In the "group represented by $R^a$—CO—CO—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—CO—$NR^e$—" can include an oxopropanamide group.

In the "group represented by $R^a$—CO—$NR^e$—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—$NR^e$—$NR^e$—" can include an acetylhydrazinyl group and an i-propylcarbonylhydrazinyl group.

In the "group represented by $R^a$—CO—$NR^e$—$NR^e$—CO—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—$NR^e$—$NR^e$—CO—" can include a 2-acetylhydrazine-1-carbonyl group.

In the "group represented by $R^b$—O—CO—O—" in G, $R^b$ represents the same meaning as that in the above "group represented by $R^b$—O—CO—".

Specific examples of the "group represented by $R^b$—O—CO—O—" can include a methoxycarbonyloxy group and an ethoxycarbonyloxy group.

In the "group represented by $R^b$—O—CO—$NR^e$—" in G, $R^b$ represents the same meaning as that in the above "group represented by "group represented by $R^b$—O—CO—". $R^e$ represents the same meaning as that in the above "group represented by $R^b$—CO—$NR^e$—".

Specific examples of the "group represented by $R^b$—O—CO—$NR^e$—" can include a methoxycarbonylamino group.

In the "group represented by $R^cR^dN$—CO—O—" in G, $R^c$ and $R^d$ represent the same meaning as those in the above "group represented by $R^cR^dN$—".

Specific examples of the "group represented by $R^cR^dN$—CO—O—" can include a carbamoyloxy group and a N,N-dimethylaminocarbonyloxy group.

In the "group represented by $R^cR^dN$—CO—$NR^e$—" in G, $R^c$ and $R^d$ represent the same meaning as those in the above "group represented by $R^cR^dN$—". $R^e$ represents the same meaning as that in the above "group represented by $R^a$—CO—$NR^e$—".

Specific examples of the "group represented by $R^cR^dN$—CO—$NR^e$—" can include a carbamoylamino group and a N,N-dimethylaminocarbonylamino group.

In the "group represented by $R^cR^dN$—CO—CO—$NR^e$—" in G, $R^c$ and $R^d$ represent the same meaning as those in the above "group represented by $R^cR^dN$—". $R^e$ represents the same meaning as that in the above "group represented by $R^a$—CO—$NR^e$—".

Specific examples of the "group represented by $R^cR^dN$—CO—CO—$NR^e$—" can include a 2-(methylamino)-2-oxoacetamide group and a 2-(t-butylamino)-2-oxoacetamide group.

In the "group represented by $R^a$—CS—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CS—$NR^e$—" can include an ethanethioamide group, a propanethioamide group, and a 2-methylpropanethioamide group.

In the "group represented by $R^cR^dN$—CS—$NR^e$—" in G, $R^c$ and $R^d$ represent the same meaning as those in the above "group represented by $R^cR^dN$—". $R^e$ represents the same meaning as that in the above "group represented by $R^a$—CO—$NR^e$—".

Specific examples of the "group represented by $R^cR^dN$—CS—$NR^e$—" can include a 3,3-dimethylthioureido group.

In the "group represented by $R^bSO_2$—$NR^e$—" in G, $R^b$ represents the same meaning as that in the above "group represented by "group represented by $R^b$—O—CO—". $R^e$ represents the same meaning as that in the above "group represented by $R^a$—CO—$NR^e$—".

Specific examples of the "group represented by $R^bSO_2$—$NR^e$—" can include a methanesulfonylamino group.

In the "group represented by $R^cR^dN$—$SO_2$—" in G, $R^c$ and $R^d$ represent the same meaning as those in the above "group represented by $R^cR^dN$—".

Specific examples of the "group represented by $R^cR^dN$—$SO_2$—" can include a N,N-dimethylaminosulfonyl group.

In the "group represented by $R^aO$—N═$CR^f$—" in G, $R^a$ represents the same meaning as that in the above "group represented by $R^a$—CO—".

$R^f$ represents a hydrogen atom, an amino group, or a substituted or unsubstituted C1-6 alkyl group.

Specific examples of the substituent in $R^f$ can include the same as those exemplified for $R^a$.

Specific examples of the "group represented by $R^aO$—N═$CR^f$—" can include a (hydroxyimino)methyl group and an (ethoxyimino)methyl group.

In the "group represented by $R^a$—C(═$NR^g$)—$NR^e$—" in G, $R^a$ represents the same meaning as that in the above "group represented by $R^a$—CO—". $R^e$ represents the same meaning as that in the above "group represented by $R^a$—CO—$NR^e$—".

Each $R^9$ independently represents a hydrogen atom, a substituted or unsubstituted C1-6 alkyl group, or a substituted or unsubstituted C6-10 aryl group.

Specific examples of the substituent in $R^9$ can include the same as those exemplified for $R^a$.

In the "group represented by $R^cR^dN$—C(═$NR^g$)—" in G, $R^c$ and $R^d$ represent the same meaning as those in the above "group represented by $R^cR^dN$—". $R^g$ represents the same meaning as that in the above "group represented by $R^a$—C(═$NR^g$)—$NR^e$—".

In the "group represented by $R^hR^iS$(═O)═N—CO—" in G, each $R^h$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group.

Specific examples of the substituent in $R^h$ or $R^i$ can include the same as those exemplified for $R^a$.

Here, $R^h$ and $R^i$ can together form a divalent organic group.

Examples of the divalent organic group that can be formed can include a substituted or unsubstituted C2-5 alkylene group or a substituted or unsubstituted C1-3 alkyleneoxy C1-3 alkylene group.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

The substituent on the "C2-5 alkylene group" or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

In the "group represented by $R^hR^iS$═N—CO—" in G, $R^h$ or $R^i$ represents the same meaning as those in the above "group represented by $R^hR^iS$(═O)═N—CO—".

In the "group represented by $R^hR^iC$═N—O—" in G, $R^h$ and $R^i$ represent the same meaning as those in the above "group represented by $R^hR^iS$═N—O—".

Specific examples of the "group represented by $R^hR^iC$═N—O—" can include a (propan-2-ylidenamino)oxy group.

When two or more substituents (G) are present, examples of a divalent organic group that can be formed together by two of the substituents can include a substituted or unsubstituted C1-5 alkylene group, a substituted or unsubstituted oxy C1-4 alkylene group, a substituted or unsubstituted oxy C2-3 alkyleneoxy group, or a substituted or unsubstituted C1-3 alkyleneoxy C1-3 alkylene group.

Examples of the "C1-5 alkylene group" can include a methylene group, a dimethylene group, a trimethylene group, and a tetramethylene group.

Examples of the "oxy C1-4 alkylene group" can include an oxymethylene group and an oxydimethylene group.

Examples of the "oxy C2-3 alkyleneoxy group" can include an oxydimethyleneoxy group.

Examples of the "C1-3 alkyleneoxy C1-3 alkylene group" can include a dimethyleneoxydimethylene group.

The substituent on the "C1-5 alkylene group", the "oxy C1-4 alkylene group", the "oxy C2-3 alkyleneoxy group", and the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

[Salt]

The salts of the compound are not particularly limited as long as the salts are those producible by means of organic chemistry. Examples thereof can include a salt of an inorganic acid such as hydrochloric acid and sulfuric acid; a salt of an organic acid such as acetic acid and lactic acid; a salt of an alkali metal such as lithium, sodium, and potassium; a salt of an alkaline earth metal such as calcium and magnesium; a salt of a transition metal such as iron and copper; a salt of an organic base such as triethylamine, tributylamine, pyridine, and hydrazine; and an ammonium salt.

[Production Method]

The present invention is a method for producing uracil compound, the method comprising subjecting a ureidomethylene compound to chemical reaction in the presence of an organic base or an inorganic base. The reaction scheme is as follows.

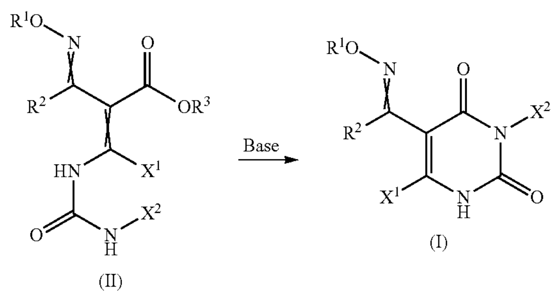

(II)

(I)

Symbols in formula (I) and formula (II) in the scheme represent the same meaning as described above. The "Base" represents an organic base or an inorganic base.

Examples of the organic base can include an amine organic base such as triethylamine, tributylamine, tetramethylethylenediamine, N,N-diisopropylamine, N,N-dimethylaniline, N,N-diethylaniline, 4-methylmorpholine, 1-azabicyclo[2.2.2]octane, 1,4-diazabicyclo[2.2.2]octane, 1,8-diazabicyclo[5.4.0]undec-7-ene, 1,5-diazabicyclo[4.3.0]non-5-ene, 7-methyl-1,5,7-triazabicyclo[4.4.0]dec-5-ene, 1,5,7-triazabicyclo[4.4.0]dec-5-ene, guanidine, 1,1,3,3-tetramethylguanidine, pyridine, 4-(dimethylamino)pyridine, 2,6-dimethylpyridine, and picoline.

The amount of usage of the organic base is, for example, 0.5 to 8.0 mol, and preferably 2.0 to 4.0 mol to the ureidomethylene compound (1 mol).

Examples of the inorganic base include lithium carbonate, lithium hydrogen carbonate, sodium carbonate, sodium hydrogen carbonate, potassium carbonate, potassium hydrogen carbonate, cesium carbonate, lithium acetate, sodium acetate, potassium acetate, sodium formate, potassium formate, calcium formate, trisodium phosphate, tripotassium phosphate, lithium hydroxide, sodium hydroxide, potassium hydroxide, cesium hydroxide, calcium hydroxide, barium hydroxide, sodium hydride, and potassium hydride; sodium methoxide, sodium ethoxide, lithium t-butoxide, sodium t-butoxide, and potassium t-butoxide.

The amount of usage of the inorganic base is, for example, 0.5 to 8.0 mol, and preferably 2.0 to 4.0 mol to the ureidomethylene compound (1 mol).

The chemical reaction can be performed without any solvent, or in a solvent. In particular, if the ureidomethylene compound is liquid at a temperature in the chemical reaction, no solvent can be used. It is preferable in view of operability to perform the chemical reaction in an organic solvent, though the reaction proceeds even in an aqueous solvent. The organic solvent is not particularly limited as long as the organic solvent is inert to the ureidomethylene compound. Examples of the organic solvent can include an ether such as diethyl ether, diisopropyl ether, ethylene glycol dimethyl ether, diethylene glycol dimethyl ether, tetrahydrofuran, and 1,4-dioxane; a halogenated hydrocarbon such as dichloromethane, chloroform, 1,2-dichloroethane, chlorobenzene, and dichlorobenzene; an aliphatic hydrocarbon such as pentane, hexane, cyclohexane, heptane, and octane; an aromatic hydrocarbon such as toluene, xylene, and mesitylene; a nitrile such as acetonitrile; an ester such as ethyl acetate; an aprotic polar solvent such as N,N-dimethylformamide, N,N-dimethylacetamide, dimethyl sulfoxide, N-methylpyrrolidone, 1,3-dimethyl-2-imidazolidinone, N,N'-dimethylpropyleneurea, and hexamethylphosphoric triamide, and a protic polar solvent such as methanol, ethanol, isopropanol, and ethylene glycol.

The amount of usage of the organic solvent is preferably 10 to 500 parts by mass to the ureidomethylene compound (1 part by mass).

The temperature in performing the chemical reaction is not particularly limited, and, for example, room temperature to 80° C. The reaction time is not particularly limited, and, for example, 0.5 hours to 24 hours.

After mixing the ureidomethylene compound, the organic base or inorganic base, and the organic solvent, the reaction can be progressed by stirring.

[Method for Producing Ureidomethylene Compound]

As illustrated in a reaction scheme below, the ureidomethylene compound can be prepared by allowing a compound of formula (III) to condense with a compound of formula (IV).

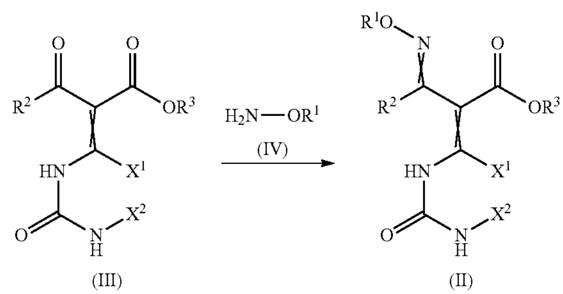
(III) (IV) (II)

$R^2$, $R^3$, $X^1$, and $X^2$ in formula (III) represent the same meaning as those in formula (II). $R^1$ in formula (IV) represents the same meaning as that in formula (II). For the compound of formula (IV), a hydrochloride thereof can be used.

For example, the compound of formula (II) can be prepared by reacting the compound of formula (III) and the compound of formula (IV) in an alcohol solvent. In this case, the reaction can be performed in the presence of a base such as pyridine.

As illustrated in a reaction scheme below, the compound of formula (III) can be prepared by allowing a compound of formula (V) to condense with a compound of formula (VI) and a compound of formula (VII).

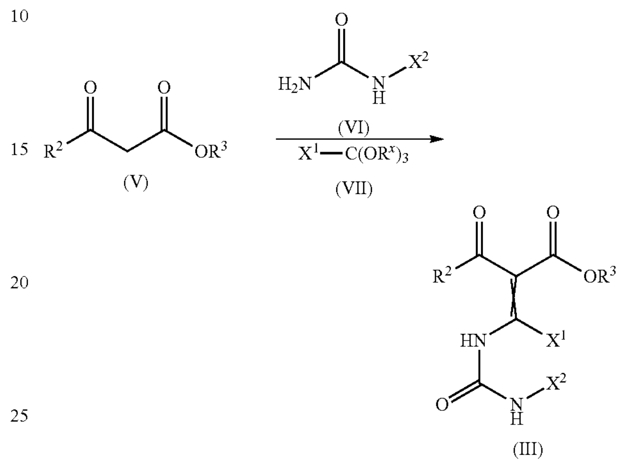
(V) (VI) (VII) (III)

$R^2$ and $R^3$ in formula (V) represent the same meaning as those in formula (II). $X^2$ in formula (VI) represents the same meaning as that in formula (II). $X^1$ in formula (VII) represents the same meaning as that in formula (II). $R^X$ represents a C1-6 alkyl group.

For example, the compound of formula (III) can be prepared by reacting the compound of formula (V) with formula (VI) and formula (VII) in the presence of a Lewis acid or a Bronsted acid without use of a solvent. Preferable is zinc(II) trifluoromethanesulfonate. For the solvent, an alcohol solvent or the like can be used.

2,6-Dioxo-3,6-dihydropyrimidine Compounds as Compounds of Formula (A)

By use of a ureide compound prepared, 2,6-dioxo-3,6-dihydropyrimidine compounds described in WO2021/085389A can be produced.

In Table 1 below, 2,6-dioxo-3,6-dihydropyrimidine compounds that can be produced are shown.

TABLE 1

| Compound number | Structural formula |
|---|---|
| I-1 | 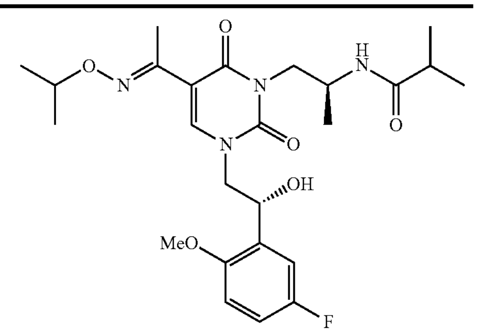 |

TABLE 1-continued
| Compound number | Structural formula |
|---|---|
| I-2 | 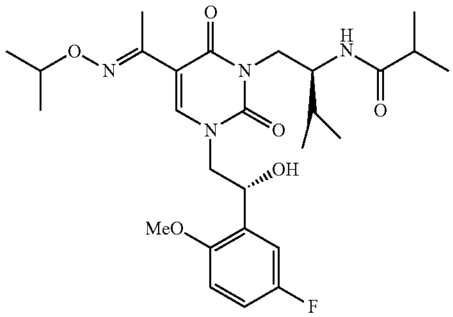 [SMILES: COc1ccc(F)cc1[C@@H](O)Cn1cc(/C(C)=N/OC(C)C)c(=O)n(C[C@@H](NC(=O)C(C)C)C(C)C)c1=O] |
| I-3 | 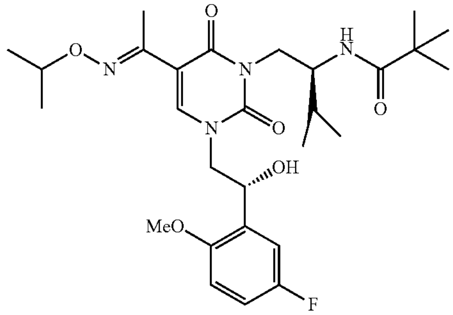 [SMILES: COc1ccc(F)cc1[C@@H](O)Cn1cc(/C(C)=N/OC(C)C)c(=O)n(C[C@@H](NC(=O)C(C)(C)C)C(C)C)c1=O] |
| I-4 | 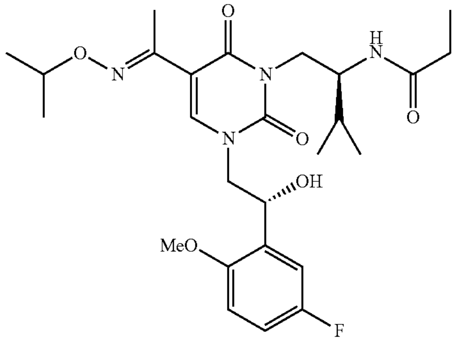 [SMILES: CCC(=O)N[C@H](Cn1c(=O)c(/C(C)=N/OC(C)C)cn(C[C@H](O)c2cc(F)ccc2OC)c1=O)C(C)C] |
| I-5 | 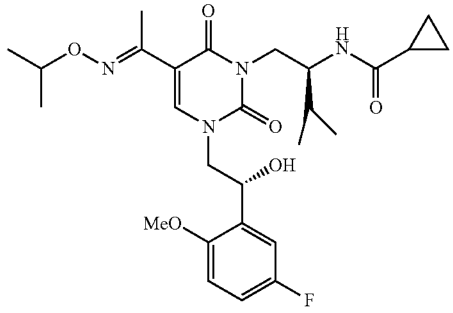 [SMILES: COc1ccc(F)cc1[C@@H](O)Cn1cc(/C(C)=N/OC(C)C)c(=O)n(C[C@@H](NC(=O)C2CC2)C(C)C)c1=O] |
TABLE 1-continued
| Compound number | Structural formula |
|---|---|
| I-6 | 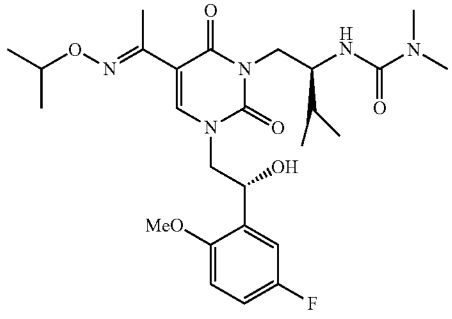 [SMILES: COc1ccc(F)cc1[C@@H](O)Cn1cc(/C(C)=N/OC(C)C)c(=O)n(C[C@@H](NC(=O)N(C)C)C(C)C)c1=O] |
| I-7 | 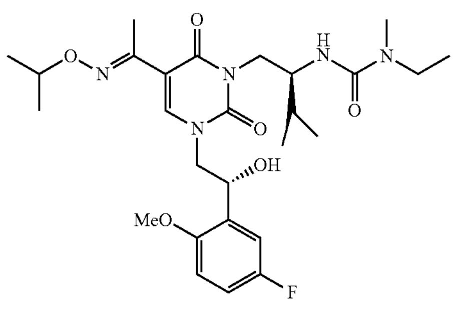 [SMILES: CCN(C)C(=O)N[C@H](Cn1c(=O)c(/C(C)=N/OC(C)C)cn(C[C@H](O)c2cc(F)ccc2OC)c1=O)C(C)C] |
| I-8 | 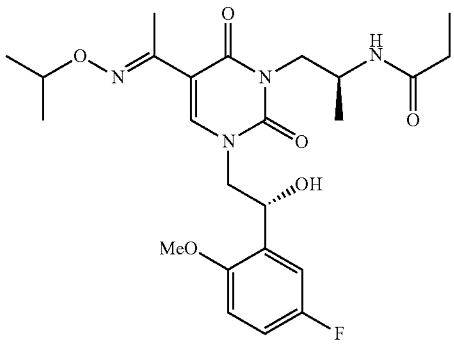 [SMILES: CCC(=O)N[C@@H](C)Cn1c(=O)c(/C(C)=N/OC(C)C)cn(C[C@H](O)c2cc(F)ccc2OC)c1=O] |
| I-9 | 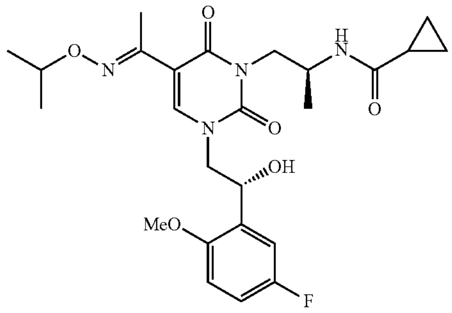 [SMILES: COc1ccc(F)cc1[C@@H](O)Cn1cc(/C(C)=N/OC(C)C)c(=O)n(C[C@H](C)NC(=O)C2CC2)c1=O] |

TABLE 1-continued
| Compound number | Structural formula |
| --- | --- |
| I-10 | 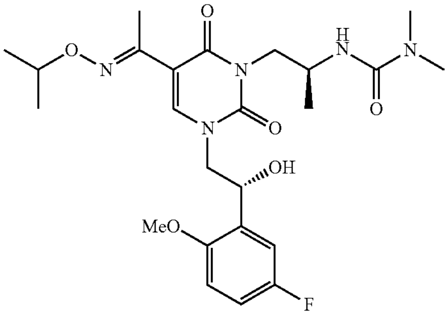 [SMILES: COc1ccc(F)cc1[C@@H](O)Cn1cc(/C(C)=N/OC(C)C)c(=O)n(C[C@H](C)NC(=O)N(C)C)c1=O] |
| I-11 | 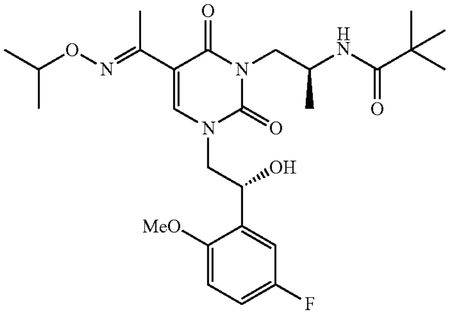 [SMILES: COc1ccc(F)cc1[C@@H](O)Cn1cc(/C(C)=N/OC(C)C)c(=O)n(C[C@H](C)NC(=O)C(C)(C)C)c1=O] |
| I-12 | 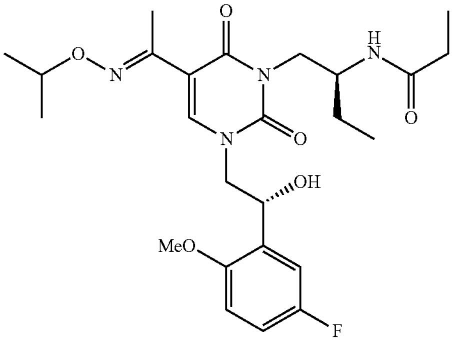 [SMILES: CCC(=O)N[C@@H](CC)Cn1c(=O)c(/C(C)=N/OC(C)C)cn(C[C@H](O)c2cc(F)ccc2OC)c1=O] |
| I-13 | 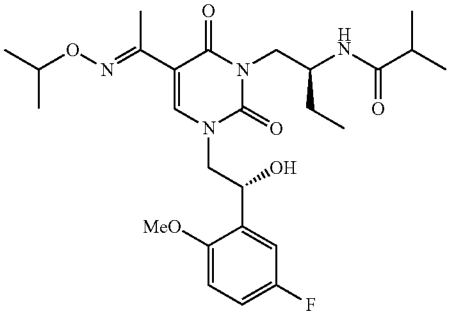 [SMILES: CC[C@@H](Cn1c(=O)c(/C(C)=N/OC(C)C)cn(C[C@H](O)c2cc(F)ccc2OC)c1=O)NC(=O)C(C)C] |
TABLE 1-continued
| Compound number | Structural formula |
| --- | --- |
| I-14 | 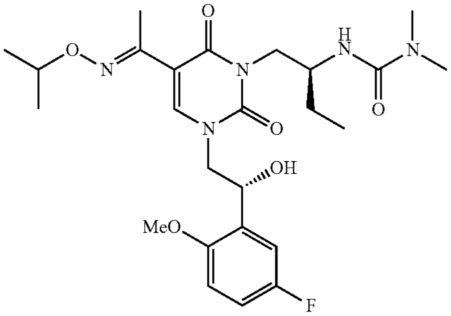 |
| I-15 | 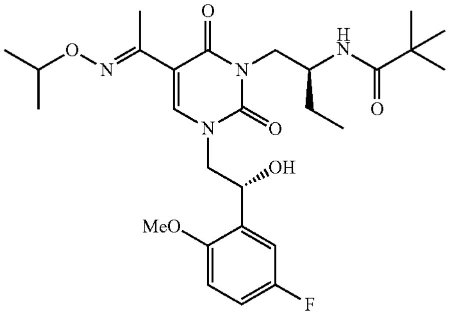 [SMILES: CC[C@@H](Cn1c(=O)c(/C(C)=N/OC(C)C)cn(C[C@H](O)c2cc(F)ccc2OC)c1=O)NC(=O)C(C)(C)C] |
| I-16 | 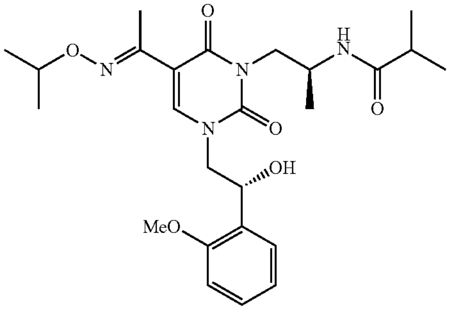 [SMILES: COc1ccccc1[C@@H](O)Cn1cc(/C(C)=N/OC(C)C)c(=O)n(C[C@H](C)NC(=O)C(C)C)c1=O] |
| I-17 | 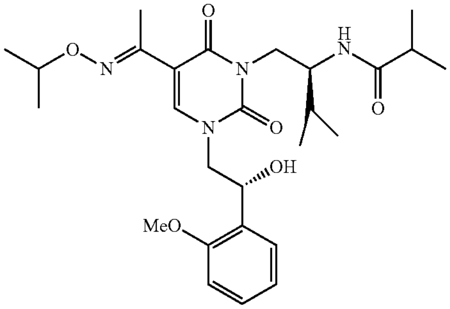 [SMILES: COc1ccccc1[C@@H](O)Cn1cc(/C(C)=N/OC(C)C)c(=O)n(C[C@@H](NC(=O)C(C)C)C(C)C)c1=O] |
| I-18 | 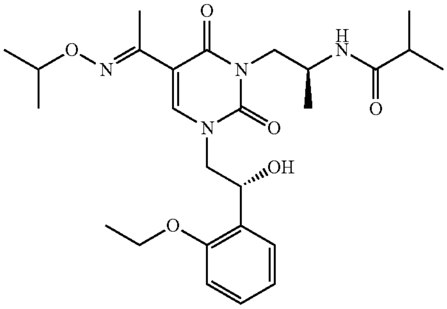 [SMILES: CCOc1ccccc1[C@@H](O)Cn1cc(/C(C)=N/OC(C)C)c(=O)n(C[C@H](C)NC(=O)C(C)C)c1=O] |

TABLE 1-continued

| Compound number | Structural formula |
|---|---|
| I-19 | 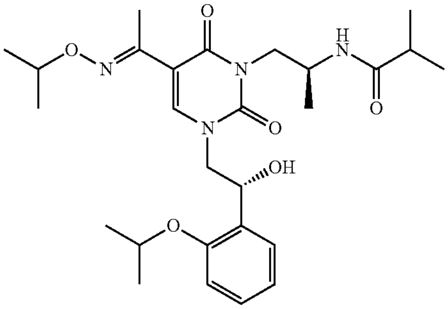 [SMILES: C/C(=N\OC(C)C)c1cn(C[C@H](O)c2ccccc2OC(C)C)c(=O)n(C[C@H](C)NC(=O)C(C)C)c1=O] |
| I-20 | 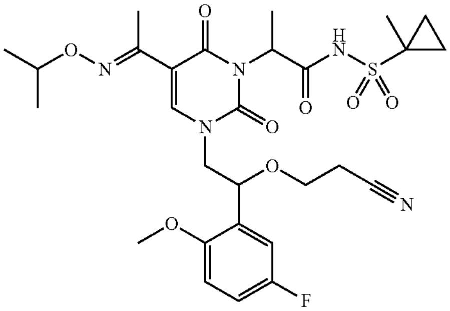 [SMILES: COc1ccc(F)cc1C(Cn1cc(/C(C)=N/OC(C)C)c(=O)n(C(C)C(=O)NS(=O)(=O)C2(C)CC2)c1=O)OCCC#N] |
| I-21 | 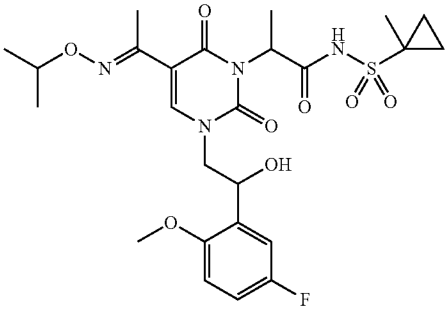 [SMILES: COc1ccc(F)cc1C(O)Cn1cc(/C(C)=N/OC(C)C)c(=O)n(C(C)C(=O)NS(=O)(=O)C2(C)CC2)c1=O] |
| I-22 | 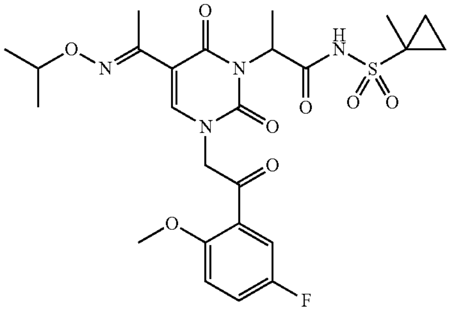 [SMILES: COc1ccc(F)cc1C(=O)Cn1cc(/C(C)=N/OC(C)C)c(=O)n(C(C)C(=O)NS(=O)(=O)C2(C)CC2)c1=O] |

TABLE 1-continued

| Compound number | Structural formula |
|---|---|
| I-23 | 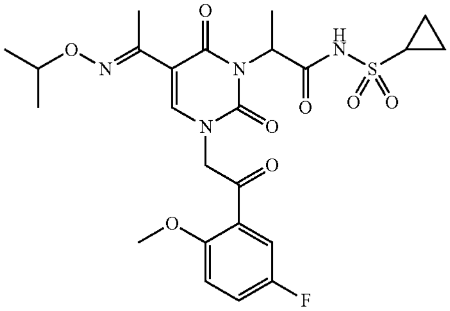 [SMILES: COc1ccc(F)cc1C(=O)Cn1cc(/C(C)=N/OC(C)C)c(=O)n(C(C)C(=O)NS(=O)(=O)C2CC2)c1=O] |
| I-24 | 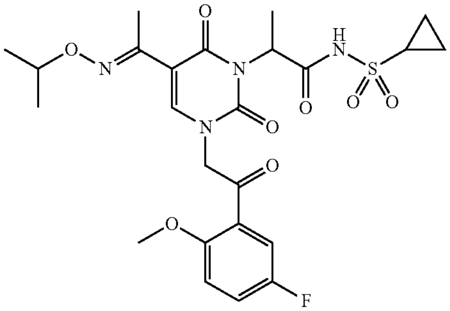 [SMILES: COc1ccc(F)cc1C(=O)Cn1cc(/C(C)=N/OC(C)C)c(=O)n(C(C)C(=O)NS(=O)(=O)C2CC2)c1=O] |

For some of the compounds in Table 1, the melting points are shown. For each of them, a low-melting-point compound and a high-melting-point compound existed.

Compound number I-1: lower melting point (65 to 68° C.), higher melting point (121 to 124° C.)

Compound number I-2: lower melting point (91 to 92° C.), higher melting point (121 to 123° C.)

Compound number I-3: lower melting point (69 to 70° C.), higher melting point (88 to 90° C.)

Furthermore, for some of the compounds, the melting points are shown.

Compound number I-20: melting point (129 to 130° C.)

Compound number I-21: melting point (121 to 122° C.)

Compound number I-22: melting point (127 to 128° C.)

Compound number I-23: melting point (105 to 106° C.)

Compound number I-24: melting point (112 to 113° C.)

The present invention will be more specifically described by showing Examples. The present invention is not limited by Examples in the following.

Example 1

Synthesis of (E)-5-(1-(isopropoxyimino)ethyl)pyrimidine-2,4(1H,3H)-dione

(Step 1) Synthesis of ethyl 3-oxo-2-(ureidomethylene)butanoate

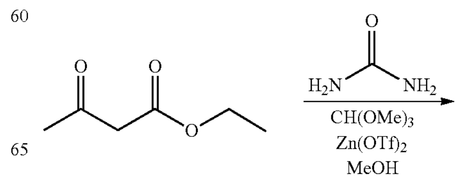

-continued

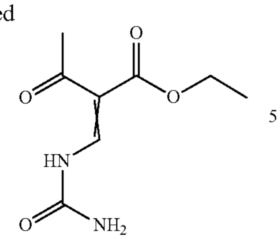

Urea (720 g) was dissolved in ethyl acetoacetate (1.28 kg) and trimethyl orthoformate (1.05 kg), zinc(II) trifluoromethanesulfonate (181 g) was added thereto, the resultant was stirred at room temperature (23° C.) for 8 hours, methanol (0.50 L) was then added thereto, and the resultant was stirred at room temperature (23° C.) over two nights.

Water was added to the reaction solution, which was stirred for 2 hours, and crystals were then taken out by filtration. Thereafter, the crystals were washed twice with water and hexane to afford the title compound (1.84 kg). Yield: 92%.

(Step 2) Synthesis of ethyl 3-(isopropoxyimino)-2-(ureidomethylene)butanoate

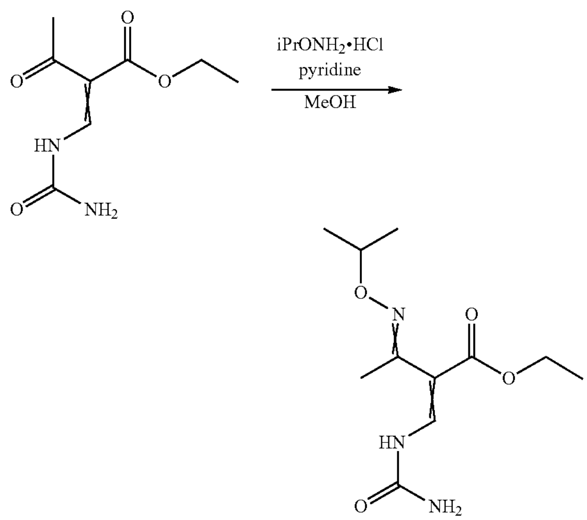

Ethyl 3-oxo-2-(ureidomethylene)butanoate (1.0 g) was dissolved in methanol (25 mL), pyridine (443 μL) and 0-isopropylhydroxylamine hydrogen chloride (614 mg) were added thereto, and the resultant was stirred at room temperature (23° C.) overnight.

After adding 1 N aqueous solution of hydrochloric acid, extraction was performed with chloroform, and the extract was dried over sodium sulfate. The solvent was distilled off under reduced pressure to afford the title compound (1.0 g). Yield: quant.

The following shows NMR data of the resulting title product.

$^1$H-NMR ($CDCl_3$) δ: 11.38 (0.01H, d, J=12.6 Hz), 9.84 (0.40H, d, J=12.2 Hz), 9.71 (0.01H, d, J=11.9 Hz), 9.05 (0.29H, d, J=12.5 Hz) 8.57 (0.40H, d, J=4.2 Hz) 8.44 (0.01H, d, J=12.6 Hz), 7.99 (0.29H, d, J=12.2 Hz), 7.80-7.76 (0.29H, m), 7.50 (0.40H, d, J=12.2 Hz), 7.40-7.36 (0.49H, m), 7.08-7.04 (0.01H, m), 7.00 (1.00H, brs), 6.85 (0.40H, brs), 4.46-4.08 (3.00H, m), 1.95 (1.35H, s), 1.92 (1.25H, s), 1.87 (0.37H, s), 1.80 (0.03H, s), 1.27-1.05 (9.00H, m).

(Step 3) Synthesis of (E)-5-(1-(isopropoxyimino) ethyl)pyrimidine-2,4(1H,3H)-dione

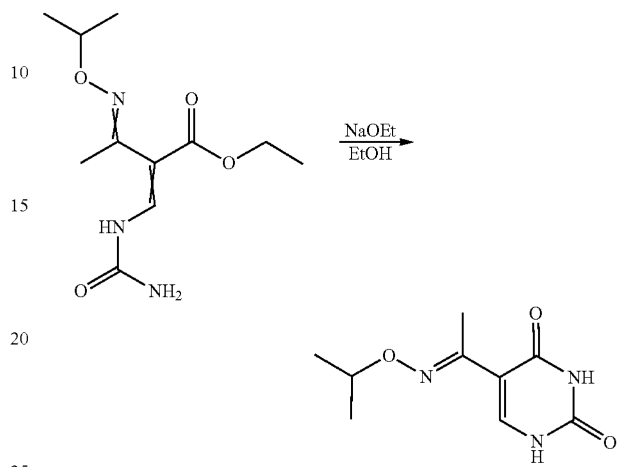

Ethyl 3-(isopropoxyimino)-2-(ureidomethylene)butanoate (1.0 g) was dissolved in ethanol (25 mL), 2 N ethanol solution of sodium ethoxide (5.0 mL) was added dropwise thereto under ice cooling, and the resultant was then stirred at room temperature (23° C.) overnight.

After 1 N aqueous solution of hydrochloric acid was added to the reaction liquid, extraction was performed with chloroform, and the extract was dried over sodium sulfate.

The solvent was distilled off under reduced pressure, and recrystallization was performed with methanol to afford the title compound (895 mg). Yield: 85%.

The following shows NMR data of the resulting title product.

$^1$H-NMR (DMSO) δ: 11.24 (1.00H, brs), 11.10 (1.00H, brs), 7.42 (1.00H, d, J=2.8 Hz), 4.28 (1.00H, dq, J=6.4 Hz), 1.99 (3.00H, s), 1.20 (6.00H, d, J=6.4 Hz).

Example 2

Synthesis of (E)-5-(1-(isopropoxyimino)ethyl)pyrimidine-2,4(1H,3H)-dione (Step 1) Synthesis of methyl 3-oxo-2-(ureidomethylene)butanoate

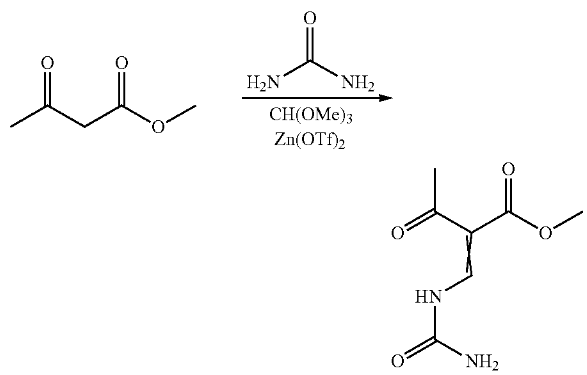

Urea (6.20 g) was dissolved in methyl acetoacetate (10.0 g) and trimethyl orthoformate (10.0 g), zinc(II) trifluoromethanesulfonate (1.56 g) was added thereto, and the resultant was stirred at room temperature (23° C.) for 3 days. Water was added to the reaction solution, which was stirred for 2 hours, and crystals were taken out by filtration. Thereafter, the crystals were washed with water and hexane to afford the title compound (11.6 g). Yield: 72%.

The following shows NMR data of the resulting title product.

$^1$H-NMR (DMSO) δ: 11.39 (0.61H, d, J=12.6 Hz), 10.13-10.11 (0.31H, m) 8.47-8.40 (0.86H, m), 7.72 (0.69H, brs), 7.52 (0.25H, brs), 7.30 (0.83H, brs), 6.80 (0.45H, brs), 3.78 (0.40H, s), 3.70 (1.70H, s), 3.59 (0.90H, s), 2.41 (2.42H, s), 2.34 (0.13H, s), 2.25 (0.45H, s).

(Step 2) Synthesis of methyl 3-(isopropoxyimino)-2-(ureidomethylene)butanoate

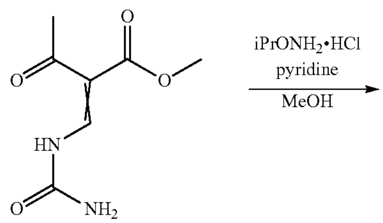

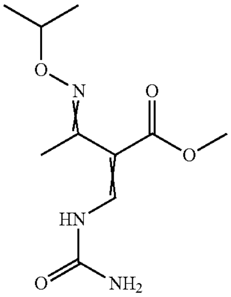

Methyl 3-oxo-2-(ureidomethylene)butanoate (465 mg) was dissolved in methanol (25 mL), pyridine (237 μL) and 0-isopropylhydroxylamine hydrogen chloride (333 mg) were added thereto, and the resultant was stirred at room temperature (23° C.) overnight.

After adding 1 N aqueous solution of hydrochloric acid, extraction was performed with chloroform, and the extract was dried over sodium sulfate. The solvent was distilled off under reduced pressure to afford 606 mg of the title product. Yield: quant.

The following shows NMR data of the resulting title product.

$^1$H-NMR (DMSO) δ: 11.90 (0.07H, d, J=7.1 Hz), 10.00-9.88 (0.72H, m), 8.63-8.55 (0.05H, m), 8.16-7.97 (0.22H, m), 7.66-7.46 (0.43H, m), 5.34 (0.13H, brs), 4.97 (0.94H, brs), 4.81 (0.44H, brs), 4.38-4.27 (1.00H, m), 3.80-3.70 (3.00H, m), 2.14 (0.80H, s), 1.99 (1.40H, s), 1.97 (0.33H, s), 1.91 (0.47H, s), 1.31-1.16 (6.00H, m).

(Step 3) Synthesis of (E)-5-(1-(isopropoxyimino)ethyl)pyrimidine-2,4(1H,3H)-dione

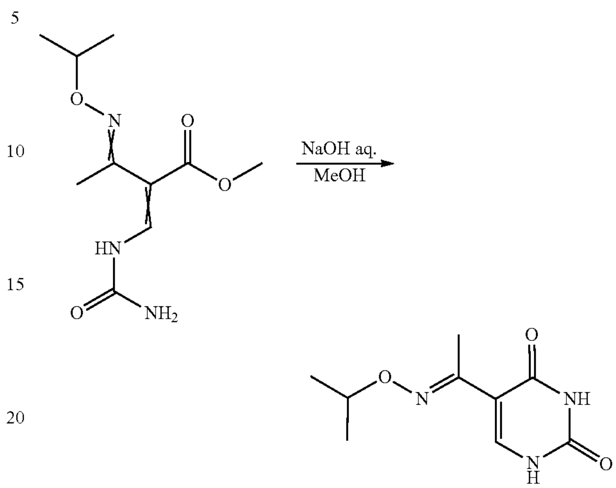

Methyl 3-(isopropoxyimino)-2-(ureidomethylene)butanoate (606 mg) was dissolved in methanol (25 mL), 6 N aqueous solution of sodium hydroxide (3.34 mL) was added dropwise thereto under ice cooling, and the resultant was then stirred at room temperature (23° C.) overnight.

After adding 1 N aqueous solution of hydrochloric acid to the reaction liquid, extraction was performed with chloroform, and the extract was dried over sodium sulfate. The solvent was distilled off under reduced pressure, and crystals were washed with hexane to afford the title compound (150 mg). Yield: 28%.

Example 3

Synthesis of (E)-5-(1-(isopropoxyimino)ethyl)pyrimidine-2,4 (1H, 3H)-dione

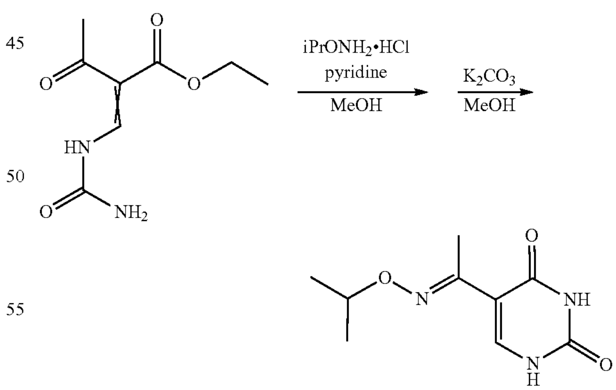

Ethyl 3-oxo-2-(ureidomethylene)butanoate (1.0 g) was dissolved in methanol (5.0 mL), pyridine (406 μL) and 0-isopropylhydroxylamine hydrogen chloride (587 mg) were added thereto, and the resultant was stirred at room temperature (23° C.) overnight.

After adding methanol (20 mL), potassium carbonate (1.38 g) was added thereto under ice cooling, and the resultant was then stirred at room temperature (23° C.)

overnight. After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (800 mg). Yield: 76%.

Example 4

Synthesis of (E)-5-(1-(isopropoxyimino)ethyl)pyrimidine-2,4 (1H, 3H)-dione

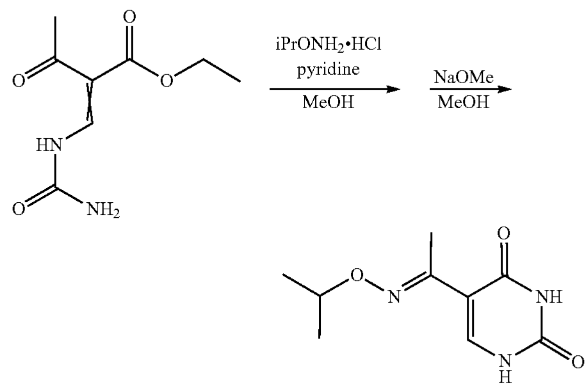

Ethyl 3-oxo-2-(ureidomethylene)butanoate (1.0 g) was dissolved in methanol (5.0 mL), pyridine (406 μL) and 0-isopropylhydroxylamine hydrogen chloride (587 mg) were added thereto, and the resultant was stirred at room temperature (23° C.) overnight.

After adding methanol (20 mL), 6 N methanol solution of sodium methoxide (1.67 mL) was added thereto under ice cooling, and the resultant was then stirred at room temperature (23° C.) overnight.

After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (801 mg). Yield: 76%.

Example 5

Synthesis of (E)-5-(1-(isopropoxyimino)ethyl)pyrimidine-2,4(1H,3H)-dione

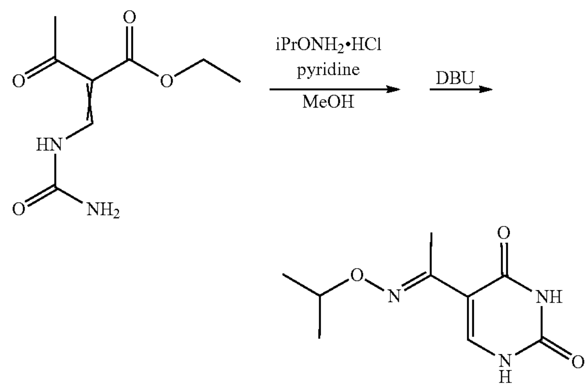

Ethyl 3-oxo-2-(ureidomethylene)butanoate (500 mg) was dissolved in methanol (2.5 mL), pyridine (232 μL) and 0-isopropylhydroxylamine hydrogen chloride (333 mg) were added thereto, and the resultant was stirred at room temperature (23° C.) overnight.

Thereafter, 1,8-diazabicyclo[5.4.0]undec-7-ene (expressed as DBU) (1.52 g) was added, and the resultant was stirred at 35° C. overnight.

After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (161 mg). Yield: 31%.

Example 6

Synthesis of (E)-5-(1-(isopropoxyimino)ethyl)pyrimidine-2,4(1H,3H)-dione

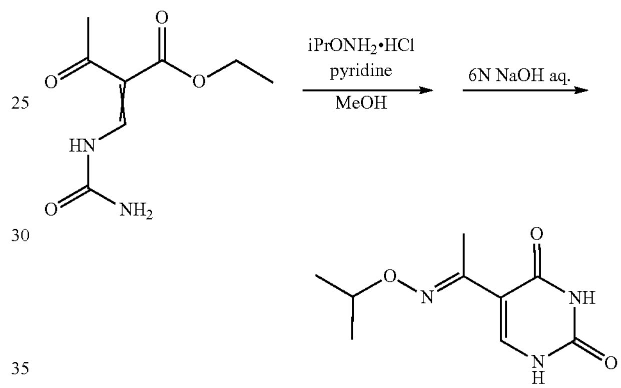

Ethyl 3-oxo-2-(ureidomethylene)butanoate (1.0 g) was dissolved in methanol (5.0 mL), pyridine (443 μL) and 0-isopropylhydroxylamine hydrogen chloride (614 mg) were added thereto, and the resultant was stirred at room temperature (23° C.) overnight.

Thereafter, 6 N aqueous solution of sodium hydroxide (3.34 mL) was added, and the resultant was then stirred at room temperature (23° C.) overnight.

After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (1.04 g). Yield: 98%.

Example 7

Synthesis of (E)-5-(1-(isopropoxyimino)ethyl)pyrimidine-2,4 (1H, 3H)-dione

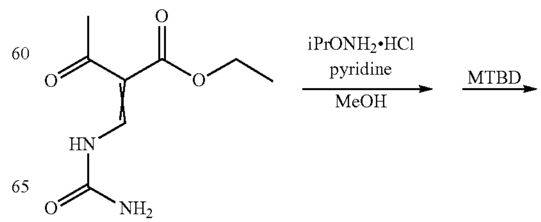

-continued

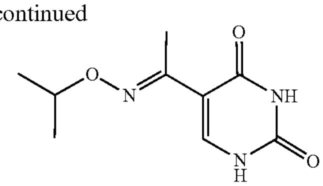

Ethyl 3-oxo-2-(ureidomethylene)butanoate (500 mg) was dissolved in MeOH (5 mL), pyridine (241 μL) and 0-isopropylhydroxylamine hydrogen chloride (335 mg) were added thereto, and the resultant was stirred at room temperature (23° C.) overnight.

After adding 7-methyl-1,5,7-triazabicyclo[4.4.0]dec-5-ene (expressed as MTBD) (765 mg), the resultant was stirred at room temperature (23° C.) overnight.

After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (430 mg). Yield: 81%.

Example 8

Synthesis of (E)-5-(1-(ethoxyimino)ethyl)pyrimidine-2,4(1H,3H)-dione

(Step 1) Synthesis of ethyl 3-(ethoxyimino)-2-(ureidomethylene)butanoate

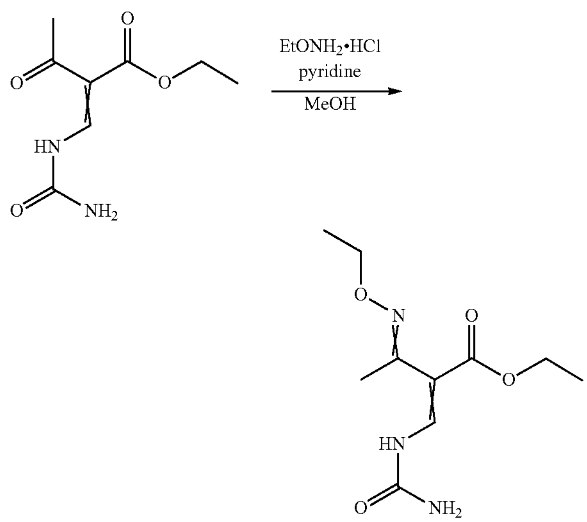

Ethyl 3-oxo-2-(ureidomethylene)butanoate (500 mg) was dissolved in methanol (2.5 mL), pyridine (241 μL) and O-ethylhydroxylamine hydrogen chloride (291 mg) were added thereto, and the resultant was stirred at room temperature (23° C.) overnight.

After adding 1 N aqueous solution of hydrochloric acid, extraction was performed with chloroform, and the extract was dried over sodium sulfate. The solvent was distilled off under reduced pressure to afford the title compound (607 mg). Yield: quant.

The following shows NMR data of the resulting title product.

$^1$H-NMR ($CDCl_3$) δ: 10.07 (0.35H, d, J=12.0 Hz), 9.92 (0.15H, d, J=11.8 Hz), 8.60 (0.03H, d, J=11.7 Hz), 8.14 (0.11H, d, J=11.5 Hz), 7.68-7.44 (0.35H, m), 4.90 (0.77H, brs), 4.78 (0.24H, brs), 4.25-4.07 (4.00H, m), 2.15-1.89 (3.00H, m), 1.35-1.19 (6.00H, m).

(Step 2) Synthesis of (E)-5-(1-(ethoxyimino)ethyl) pyrimidine-2,4(1H,3H)-dione

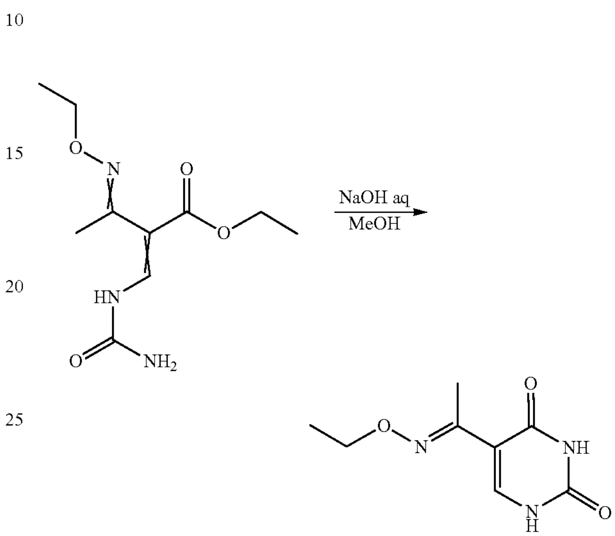

Ethyl 3-(ethoxyimino)-2-(ureidomethylene)butanoate (607 mg) was dissolved in methanol (2.5 mL), 6 N aqueous solution of sodium hydroxide (1.67 mL) was added thereto, and the resultant was then stirred at room temperature (23° C.) overnight.

After adding 1 N aqueous solution of hydrochloric acid to the reaction liquid, extraction was performed with chloroform, and the extract was dried over sodium sulfate. The solvent was distilled off under reduced pressure, and the resulting crystals were washed with hexane to afford the title compound (150 mg). Yield: 30%.

The following shows NMR data of the resulting title product.

$^1$H-NMR (DMSO) δ: 11.62 (2.00H, brs), 7.42 (1.00H, d, J=6.4 Hz), 4.06 (2.00H, t, J=6.8 Hz), 2.00 (3.00H, d, J=3.2 Hz), 1.22-1.17 (3.00H, m).

Example 9

Synthesis of (E)-3-allyl-5-(1-(isopropoxyimino) ethyl)pyrimidine-2,4(1H,3H)-dione

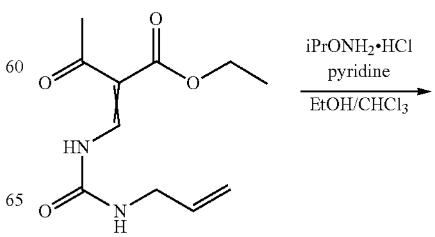

-continued

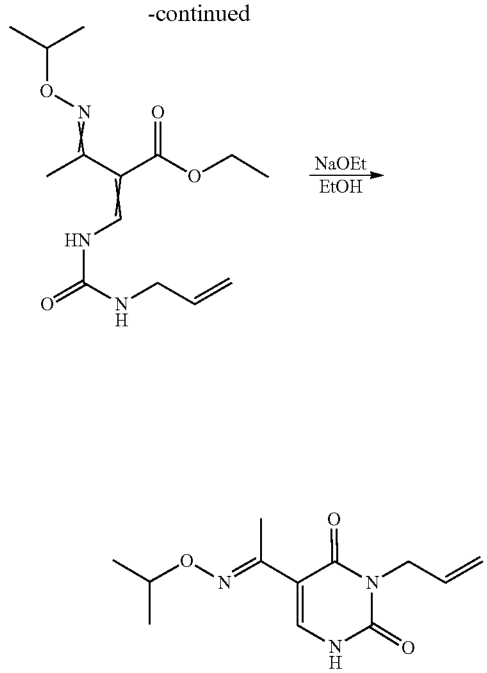

Ethyl 2-((3-allylureido)methylene)-3-oxobutanoate (1.5 g) was dissolved in a mixed solution of ethanol (31.3 mL) and chloroform (31.3 mL), pyridine (503 μL) and 0-isopropylhydroxylamine hydrogen chloride (693 mg) were added thereto, and the resultant was stirred at room temperature (23° C.) overnight.

The reaction solution was purified by silica gel column chromatography. Thereafter, the resulting residue was dissolved in ethanol (14.5 mL), 2 N ethanol solution of sodium ethoxide (4.25 mL) was added dropwise thereto under ice cooling, and the resultant was then stirred at room temperature (23° C.) overnight.

After adding saturated aqueous solution of ammonium chloride, extraction was performed with chloroform, and the extract was dried over sodium sulfate. The solvent was distilled off under reduced pressure, and purification was performed by silica gel column chromatography to afford the title compound (580 mg). Yield: 37%.

The following shows NMR date of the synthesis intermediate and the title product.

Ethyl 2-((3-allylureido)methylene)-3-(isopropoxyimino)butanoate $^1$H-NMR ($CDCl_3$) δ: 10.06 (1.00H, brs), 8.70-7.68 (1.00H, m), 5.91-5.81 (1.00H, m), 5.28-5.15 (2.00H, m), 5.00 (1.00H, brs), 4.22-4.27 (1.00H, m), 4.15-4.09 (2.00H, m), 3.92-3.90 (2.00H, m), 2.01 (3.00H, s), 1.33-1.18 (9.00H, m).

(E)-3-Allyl-5-(1-(isopropoxyimino)ethyl)pyrimidine-2,4 (1H, 3H)-dione $^1$H-NMR ($CDCl_3$) δ: 9.43 (1.00H, brs), 7.43 (1.00H, d, J=6.0 Hz), 5.93-5.83 (1.00H, m), 5.30-5.13 (2.00H, m), 4.55 (2.00H, J=6.0 Hz), 4.38-4.32 (1.00H, m), 2.15 (3.00H, s), 1.26 (6.00H, d, J=6.0 Hz).

Example 10

Synthesis of tert-butyl (S,E)-(1-(5-(1-(isopropoxyimino)ethyl)-2,6-dioxo-3,6-dihydropyrimidin-1(2H)-yl)-3-methylbutan-2-yl)carbamate

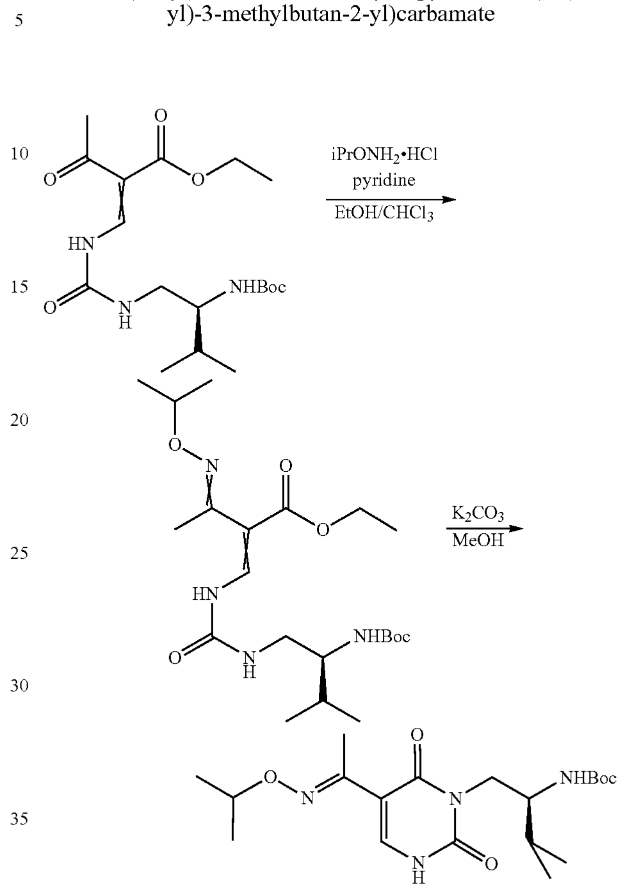

Ethyl (S)-12-acetyl-6-isopropyl-2,2-dimethyl-4,9-dioxo-3-oxa-5,8,10-triazatridec-11-en-13-oate (1.05 g) was dissolved in methanol (11.0 mL), pyridine (241 μL) and 0-isopropylhydroxylamine hydrogen chloride (334 mg) were added thereto, and the resultant was stirred at room temperature (23° C.) overnight.

After adding saturated aqueous solution of ammonium chloride, extraction was performed with chloroform, and the extract was dried over sodium sulfate. The solvent was distilled off under reduced pressure, the resultant was dissolved in methanol (11.0 mL), potassium carbonate (610 mg) was added thereto under ice cooling, and the resultant was then stirred at room temperature (23° C.) overnight.

After adding 1 N aqueous solution of hydrochloric acid, extraction was performed with chloroform, and the extract was dried over sodium sulfate. The solvent was distilled off under reduced pressure, and purification was performed by silica gel column chromatography to afford the title compound (370 mg). Yield: 32%.

"Boc" in the above scheme means a t-butoxycarbonyl group.

The following shows NMR data of the synthesis intermediate and the title product.

Ethyl (S)-12-(1-(isopropoxyimino)ethyl)-6-isopropyl-2,2-dimethyl-4,9-dioxo-3-oxa-5,8,10-triazatridec-11-en-13-oate $^1$H-NMR ($CDCl_3$) δ: 10.06-9.95 (0.45H, m), 8.62 (0.62H, d, J=4.4 Hz), 8.21 (0.22H, d, J=11.6 Hz), 7.70-7.66 (0.57H, m) 7.51-7.24 (0.50H, m), 5.86 (0.21H, brs), 5.72 (0.24H, brs), 5.11 (0.28H, brs), 4.63-4.13 (3.73H, m), 3.53-3.20 (2.97H, m), 2.18-1.91 (3.00H, m), 1.85-1.71 (1.00H, m), 1.49-1.39 (9.00H, m), 1.34-1.15 (9.02H, m), 0.98-0.90 (6.19H, m).

tert-Butyl (S,E)-(1-(5-(1-(isopropoxyimino)ethyl)-2,6-dioxo-3,6-dihydropyrimidin-1(2H)-yl)-3-methylbutan-2-yl)carbamate $^{1}$H-NMR ($CDCl_3$) δ: 9.58 (1.00H, brs), 7.41 (1.00H, d, J=5.6 Hz), 4.66 (1.00H, d, J=9.9 Hz), 4.37-4.31 (1.00H, m), 4.17-4.10 (1.00H, m), 4.00-3.83 (2.00H, m), 2.16 (3.00H, s), 1.87-1.80 (1.00H, m), 1.37-1.24 (15.0H, m), 1.01-0.98 (6.00H, m).

In the present application, particularly important uracil compounds are (E)-5-(1-(isopropoxyimino)ethyl)pyrimidine-2,4(1H,3H)-dione and (E)-5-(1-(ethoxyimino)ethyl) pyrimidine-2,4(1H,3H)-dione.

2,6-Dioxo-3,6-dihydropyrimidine Compounds

Moreover, compounds shown in Table 2 below can be produced by use of any of the ureide compounds prepared.

TABLE 2

| Compound number | Structural formula |
|---|---|
| Ia-1 | 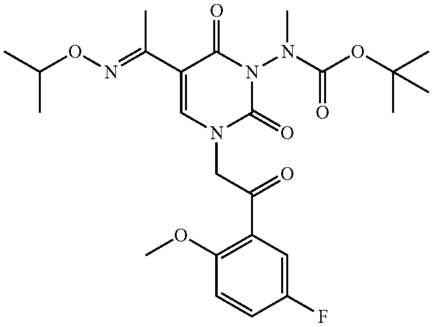 [SMILES: COc1ccc(F)cc1C(=O)Cn1cc(/C(C)=N/OC(C)C)c(=O)n(N(C)C(=O)OC(C)(C)C)c1=O] |
| Ia-2 | 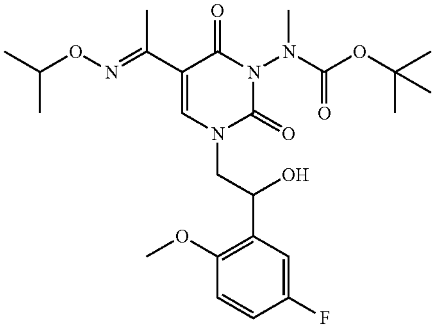 [SMILES: COc1ccc(F)cc1C(O)Cn1cc(/C(C)=N/OC(C)C)c(=O)n(N(C)C(=O)OC(C)(C)C)c1=O] |
| Ia-3 | 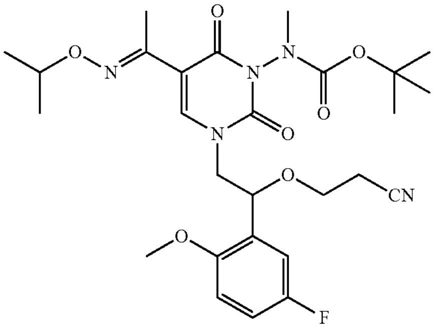 [SMILES: COc1ccc(F)cc1C(Cn1cc(/C(C)=N/OC(C)C)c(=O)n(N(C)C(=O)OC(C)(C)C)c1=O)OCCC#N] |

TABLE 2-continued

| Compound number | Structural formula |
|---|---|
| Ia-4 | 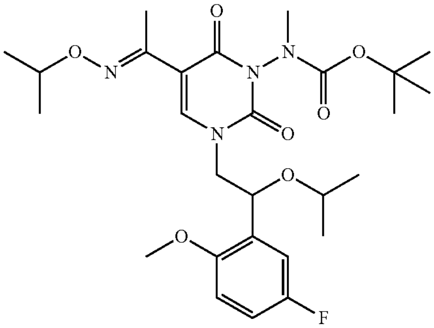 [SMILES: COc1ccc(F)cc1C(Cn1cc(/C(C)=N/OC(C)C)c(=O)n(N(C)C(=O)OC(C)(C)C)c1=O)OC(C)C] |
| Ia-5 | 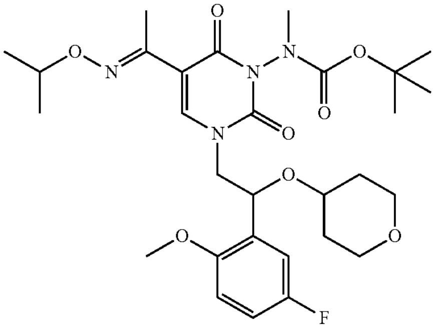 [SMILES: COc1ccc(F)cc1C(Cn1cc(/C(C)=N/OC(C)C)c(=O)n(N(C)C(=O)OC(C)(C)C)c1=O)OC1CCOCC1] |
| Ia-6 | 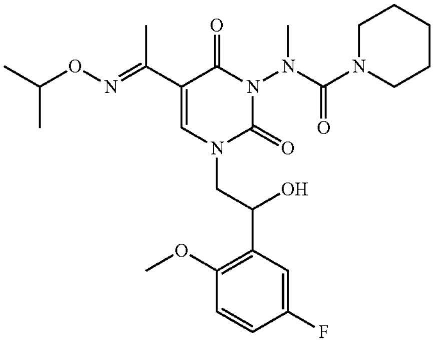 [SMILES: COc1ccc(F)cc1C(O)Cn1cc(/C(C)=N/OC(C)C)c(=O)n(N(C)C(=O)N2CCCCC2)c1=O] |
| Ia-7 | 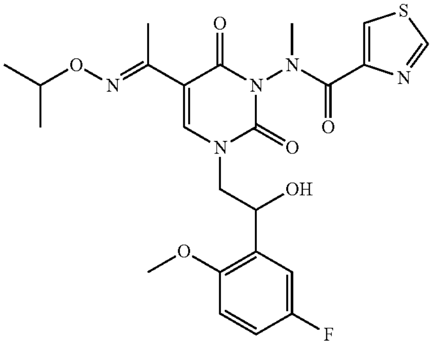 [SMILES: COc1ccc(F)cc1C(O)Cn1cc(/C(C)=N/OC(C)C)c(=O)n(N(C)C(=O)c2cscn2)c1=O] |

TABLE 2-continued

| Compound number | Structural formula |
|---|---|
| Ia-8 | 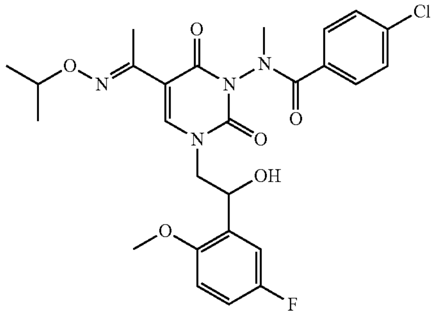 [SMILES: COc1ccc(F)cc1C(O)Cn1cc(/C(C)=N/OC(C)C)c(=O)n(N(C)C(=O)c2ccc(Cl)cc2)c1=O] |
| Ia-9 | 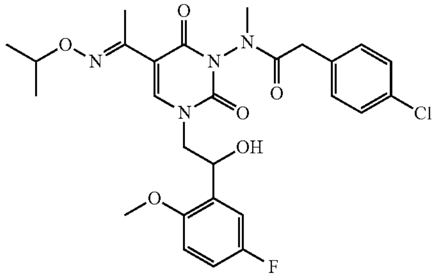 [SMILES: COc1ccc(F)cc1C(O)Cn1cc(/C(C)=N/OC(C)C)c(=O)n(N(C)C(=O)Cc2ccc(Cl)cc2)c1=O] |

The invention claimed is:

1. A method for producing a compound of formula (I) or a salt thereof:

(I)

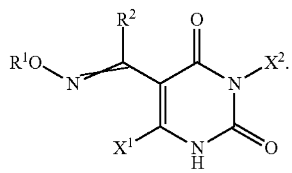

wherein in formula (I), the crossed double bond symbol represents a cis or trans double bond configuration or mixtures thereof;

$X^1$ represents a hydrogen atom or a substituted or unsubstituted C1-6 alkyl group;

$R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group;

$R^2$ represents a hydrogen atom or a substituted or unsubstituted C1-6 alkyl group;

$X^2$ represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, a substituted or unsubstituted 4 to 6-membered ring heterocyclyl group, a group represented by $R^NR^NN$—, a group represented by $R^N$—CO—$NR^N$—, a group represented by $R^N$—CO—CO—$NR^N$—, a group represented by $R^N$—O—CO—$NR^N$—, a group represented by $R^NR^NN$—CO—$NR^N$, a group represented by $R^NR^NN$—CO—CO—$NR^e$—, a group represented by $R^N$, CS—$NR^N$—, a group represented by $R^NR^NN$—CS—$NR^N$—, a group represented by $R^NSO_2$—$NR^N$—, or a group represented by $R^N$—C(=$NR^N$)—$NR^N$—;

each $R^N$ independently represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 4 to 6-membered ring heterocyclyl group, where $R^N$ and $R^N$ can together form a divalent organic group, the method comprising:

subjecting a compound of formula (II) or a salt thereof to chemical reaction in the presence of an organic base or an inorganic base:

(II)

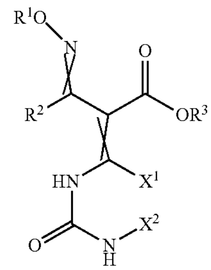

wherein in formula (II), the crossed double bond symbol represents a cis or trans double bond configuration or mixtures thereof, $R^1$, $R^2$, $X^1$, and $X^2$ represent the same meaning as those in formula (I)

$R^3$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, or a substituted or unsubstituted C6-10 aryl group.

2. The method according to claim 1, wherein a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group in $X^2$ and $R^N$ is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^cR^dN$—, a group represented by $R^cR^aN$—CO—, a group represented by $R^cR^dN$—$NR^d$—CO—, a group represented by $R^bSO_2$—$NR^d$—CO—, a group represented by $R^a$—CO—O—, a group represented by $R^a$—CO—$NR^e$—, a group represented by $R^a$—CO—CO—$NR^e$—, a group represented by $R^a$—CO—$NR^e$—$NR^e$—, a group represented by $R^a$—CO—$NR^e$—$NR^e$—CO—, a group represented by $R^b$—O—CO—O—, a group represented by $R^b$—O—CO—$NR^e$—, a group represented by $R^cR^dN$—CO—O—, a group represented by $R^cR$ N—CO—$NR^e$—, a group represented by $R^cR^dN$—CO—CO—$NR^e$—, a group represented by $R^a$—CS—$NR^e$—, a group represented by $R^cR$ N—CS—$NR^e$—, a group represented by $R^bSO_2$—$NR^e$—, a group represented by $R^cR$ N—$SO_2$—, a group represented by $R^aO$—N═$CR^f$—, a group represented by $R^hR^iC$═N—O—, a group represented by $R^a$—C(═$NR^g$)—$NR^e$—, a group represented by $R^cR^dON$—C(═$NR^g$)—, a group represented by $R^hR^iS$(═O)═N—CO—, and a group represented by $R^hR^iS$═N—CO—;

each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group, each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^e$ and $R^d$ can together form a divalent organic group, each $R^e$ independently represents a hydrogen atom, a substituted or unsubstituted C1-6 alkyl group, a substituted or unsubstituted C1-6 alkoxy group, or a substituted or unsubstituted C6-10 aryl group, $R^f$ represents a hydrogen atom, an amino group, or a substituted or unsubstituted C1-6 alkyl group, each $R^g$ independently represents a hydrogen atom, a substituted or unsubstituted C1-6 alkyl group, or a substituted or unsubstituted C6-10 aryl group, each $R^h$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group, where $R^h$ and $R^i$ can together form a divalent organic group; and when two or more substituents are present on the linear C1-6 alkyl group, two of the substituents can together form a divalent organic group.

3. A compound of formula (II) or a salt thereof:

(II)

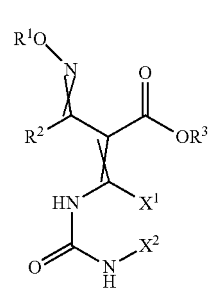

wherein in formula (II), the crossed double bond symbol represents a cis or trans double bond configuration or mixtures thereof;

$X^1$ represents a hydrogen atom or a substituted or unsubstituted C1-6 alkyl group;

$R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group;

$R^2$ represents a hydrogen atom or a substituted or unsubstituted C1-6 alkyl group;

$X^2$ represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, a substituted or unsubstituted 4 to 6-membered ring heterocyclyl group, a group represented by $R^NR^NN$—, a group represented by $R^N$—CO—$NR^N$—, a group represented by $R^N$—CO—CO—$NR^N$, a group represented by $R^N$—O—CO—$NR^N$—, a group represented by $R^NR^NN$—CO—$NR^N$, a group represented by $R^NR^NN$—CO—CO—$NR^e$—, a group represented by $R^N$—CS—$NR^N$—, a group represented by $R^NR^NN$—CS—$NR^N$—, a group represented by $R^NSO_2$—$NR^N$—, or a group represented by $R^N$—C(═$NR^N$)—$NR^N$—;

each $R^N$ independently represents a hydrogen atom, a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 4 to 6-membered ring heterocyclyl group, where $R^N$ and $R^N$ can together form a divalent organic group; and $R^3$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, or a substituted or unsubstituted C6-10 aryl group.

4. The compound according to claim 3 or a salt thereof, wherein a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group in $X^2$ and $R^N$ is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^c$R N—, a group represented by $R^c$R N—CO—, a group represented by $R^cR^d$N—$NR^d$—CO—, a group represented by $R^bSO_2$—$NR^c$—CO—, a group represented by $R^a$—CO—O—, a group represented by $R^a$—CO—$NR^e$—, a group represented by $R^a$—CO—CO—$NR^e$—, a group represented by $R^a$—CO—$NR^e$—$NR^e$—, a group represented by $R^a$—CO—$NR^e$—$NR^e$—CO—, a group represented by $R^b$, O—CO—O—, a group represented by $R^b$—O—CO—$NR^e$—, a group represented by $R^cR^a$N—CO—O—, a group represented by $R^c$R N—CO—$NR^e$—, a group represented by $R^cR^a$N—CO—CO—$NR^e$—, a group represented by $R^a$—CS—$NR^e$—, a group represented by $R^c$R N—CS—$NR^e$—, a group represented by $R^bSO_2$—$NR^e$—, a group represented by $R^cR^d$N—$SO_2$—, a group represented by $R^a$O—N═$CR^f$—, a group represented by $R^hR^i$C═N—O—, a group represented by $R^a$—C(═$NR^g$)—$NR^e$—, a group represented by $R^cR^d$N—C(═$NR^g$)—, a group represented by $R^hR^i$S(—O)═N—CO—, and a group represented by $R^hR^i$S—N—CO—;

each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group, each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^e$ and $R^d$ can together form a divalent organic group, each $R^e$ independently represents a hydrogen atom, a substituted or unsubstituted C1-6 alkyl group, a substituted or unsubstituted C1-6 alkoxy group, or a substituted or unsubstituted C6-10 aryl group, $R^f$ represents a hydrogen atom, an amino group, or a substituted or unsubstituted C1-6 alkyl group, each $R^g$ independently represents a hydrogen atom, a substituted or unsubstituted C1-6 alkyl group, or a substituted or unsubstituted C6-10 aryl group, each $R^h$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group, where $R^h$ and $R^1$ can together form a divalent organic group; and when two or more substituents are present on the linear C1-6 alkyl group, two of the substituents can together form a divalent organic group.

* * * * *